United States Patent
Bolduc et al.

(10) Patent No.: US 6,254,615 B1
(45) Date of Patent: Jul. 3, 2001

(54) SURGICAL CLIPS AND METHODS FOR TISSUE APPROXIMATION

(75) Inventors: Lee R. Bolduc, Mountain View; Hanson S. Gifford, III, Woodside; James I. Fann, Los Altos, all of CA (US)

(73) Assignee: Heartport, Inc., Redwood City, CA (US)

(*) Notice: Subject to any disclaimer, the term of this patent is extended or adjusted under 35 U.S.C. 154(b) by 0 days.

(21) Appl. No.: 09/420,609

(22) Filed: Oct. 18, 1999

Related U.S. Application Data

(63) Continuation of application No. 08/598,513, filed on Feb. 8, 1996, now Pat. No. 5,976,159, which is a continuation-in-part of application No. 08/394,333, filed on Feb. 24, 1995.

(51) Int. Cl.⁷ .................................................. A61B 17/04
(52) U.S. Cl. .............................................. 606/142; 606/151
(58) Field of Search .................................... 606/151, 157, 606/158, 220, 221, 228, 230, 139, 213, 104, 142, 143

(56) References Cited

U.S. PATENT DOCUMENTS

| | | |
|---|---|---|
| 1,756,670 | 4/1930 | Treat . |
| 3,254,650 | 6/1966 | Collito . |
| 3,254,651 | 6/1966 | Collito . |
| 3,519,187 | 7/1970 | Kapitanov et al. . |
| 3,570,497 | 3/1971 | Lemole . |
| 3,774,615 | 11/1973 | Lim et al. . |
| 4,350,160 | 9/1982 | Kolesov et al. . |
| 4,352,358 | 10/1982 | Angelchik . |
| 4,366,819 | 1/1983 | Kaster . |
| 4,368,736 | 1/1983 | Kaster . |
| 4,505,414 | 3/1985 | Filipi . |

(List continued on next page.)

FOREIGN PATENT DOCUMENTS

WO 97/40754 11/1997 (WO).

OTHER PUBLICATIONS

Androsov, P.I. "New Method of Surgical Treatment of Blood Vessel Lesions", *Arch Surg*. 73:902–910 (1956).

Vogelfanger et al., "A Concept of Automation in Vascular Surgery: A Preliminary Report on a Mechanical Instrument for Arterial Anastomosis" *Can. J. of Surg* 1:262–265 (1958).

Inokuchi, K. "A New Type of Vessel–Suturing Apparatus" *Arch Surg*. 77:954–957 (1958).

Rohman et al. Chapter IX—Cardiovascular Technique "Double Coronary Artery–Internal Mammary Artery Anastomoses, Tantalum Ring Technique" *Surg. Forum* 11:236 (1960).

Holt et al. "A New Technique for End–To–End Anastomosis of Small Arteries" *Surg. Forum* 11:242 (1960).

(List continued on next page.)

*Primary Examiner*—Gary Jackson
(74) *Attorney, Agent, or Firm*—Jens E. Hoekendijk

(57) ABSTRACT

Surgical clips, and methods of use thereof, are provided for tissue approximation and attachment, and more particularly, for sealingly joining a graft vessel to a target vessel. The graft vessel has a free end and a graft vessel wall defining a graft lumen. The target vessel has a target vessel wall defining a target lumen and has an opening in the target vessel wall. The anastomosis clip includes a clip body having a distal extremity with a distal end and a proximal extremity with a proximal end. The distal end is configured to penetrate through the graft vessel wall near the free end and through the target vessel wall near the opening such that both the distal and proximal ends of the clip body are outside the graft and target vessels. At least a portion of the clip body is shapable so as to compress the graft vessel wall against the target vessel wall with the target vessel lumen in communication with the graft vessel lumen.

48 Claims, 17 Drawing Sheets

U.S. PATENT DOCUMENTS

| | | |
|---|---|---|
| 4,523,592 | 6/1985 | Daniel . |
| 4,553,542 | 11/1985 | Schenck et al. . |
| 4,593,693 | 6/1986 | Schenck . |
| 4,607,637 | 8/1986 | Berggren et al. . |
| 4,624,255 | 11/1986 | Schenck et al. . |
| 4,624,257 | 11/1986 | Berggren et al. . |
| 4,657,019 | 4/1987 | Walsh et al. . |
| 4,665,906 | 5/1987 | Jervis . |
| 4,747,407 | 5/1988 | Liu et al. . |
| 4,809,695 * | 3/1989 | Gwathmey et al. .................. 606/142 |
| 4,907,591 | 3/1990 | Vasconcellos et al. . |
| 4,917,087 | 4/1990 | Walsh et al. . |
| 4,917,090 | 4/1990 | Berggren et al. . |
| 4,917,091 | 4/1990 | Berggren et al. . |
| 4,935,028 * | 6/1990 | Drews .................................. 606/220 |
| 5,119,983 | 6/1992 | Green et al. . |
| 5,234,447 | 8/1993 | Kaster et al. . |
| 5,330,503 * | 7/1994 | Yoon .................................... 606/223 |
| 5,336,233 | 8/1994 | Chen . |
| 5,366,462 | 11/1994 | Kaster et al. . |
| 5,478,354 | 12/1995 | Tovey et al. . |
| 5,522,834 | 6/1996 | Fonger et al. . |
| 5,549,619 | 8/1996 | Peters et al. . |
| 5,554,162 | 9/1996 | DeLange . |
| 5,620,452 | 4/1997 | Yoon . |
| 5,695,504 | 12/1997 | Gifford, III et al. . |
| 5,702,412 | 12/1997 | Popov et al. . |

OTHER PUBLICATIONS

Goetz et al. "Internal Mammary–Coronary Artery Anastomosis—A Nonsuture Method Employing Tantalum Rings" . *Thorac Cardiac Surg* 41:378–386 (1961).

Inokuchi, K. "Stapling Device for End–to–Side Anastomosis of Blood Vessel" *Arch. Surg.* 82:337–341 (1961).

Nakayama et al. A simple new apparatus for small vessel anastomosis (free autograft of the sigmoid included) *Surgery* 52(6):918–931 (1962).

Cooper et al. "Development of the Surgical Stapler with Emphasis on Vascular Anastomosis" *Transactions—The New York Academy of Sciences*, 23:365–377 (1963).

Miller, T.R. "The Russian Stapling Device" *Transactions—The New York Academy of Sciences* 25:378–381 (1963).

Narter et al. "An Experimental Method for Nonsuture Anastomosis of the Aorta" *Surg. Gyn. Obstet* 119:362–364 (1964).

Gottlob et al. "Anastomoses of small arteries and veins by means of bushings and adhesive" *J. Cardiac Surg* 9:337–341 (1968).

Guyton et al. "A Mechanical Device for Sutureless Aorta–Saphenous Vein Anastomosis" *Ann Thorac Surg* 28:342–345 (1979).

Gentili et al. A Technique for Rapid Non–Suture Vascular Anastomosis *Can J Neurol Sci* 14:92–95 (1987).

Olearchyk, A.S. "Vasilii I. Kolesov—A pioneer of coronary revascularization by internal mammary–coronary artery grafting" *J. Thorac Cardiovasc Surg* 96:13–18 (1988).

Ragnarsson et al. "Microvenous End–To–Side Anastomosis: An Experimental Study Comparing the Unilink System and Sutures" *J Reconstr Microsurg* 5(3):217–224 (1989).

Ragnarsson et al. "Arterial End–to–Side Anastomosis with the Unilink System" *Ann Plastic Surg* 22(5):405–415 (1989).

Li et al. "End–To–Side Anastomosis in the Dog Using the 3M Precise Microvascular Anastomotic System: A Comparative Study" *J. Reconstr Microsurg* 7(4):345–350 (1991).

Lanzetta et al. "Long–term Results of 1 millimeter Arterial Anastomisis Using the 3M Precise Microvascular Anastomotic System" *Microsurg* 13:313–320 (1992).

Berggren et al. "Clinical Experience with the Unilink/3M Precise Microvascular Anastomotic Device" *Scand J Plast Reconstr Hand Surg* 27:35–39 (1993).

* cited by examiner

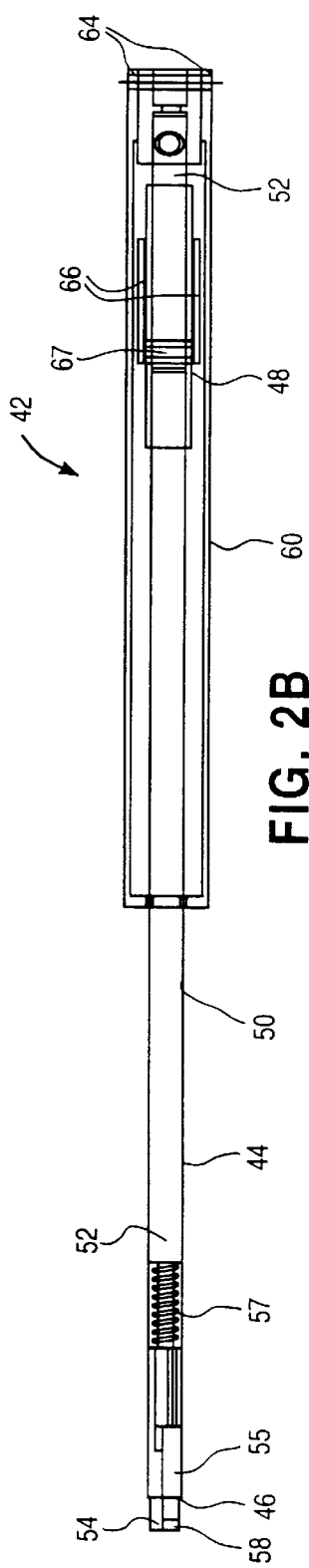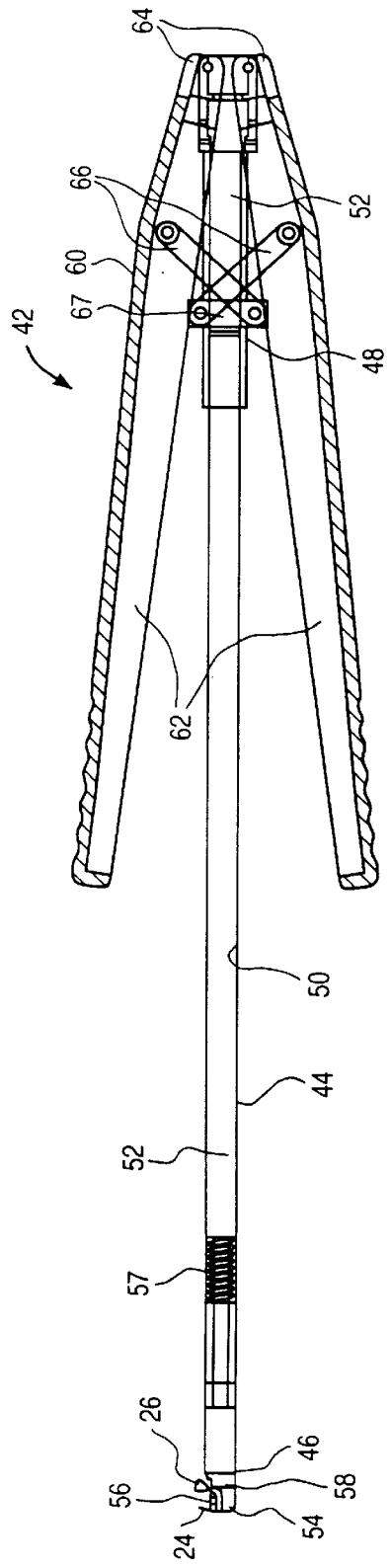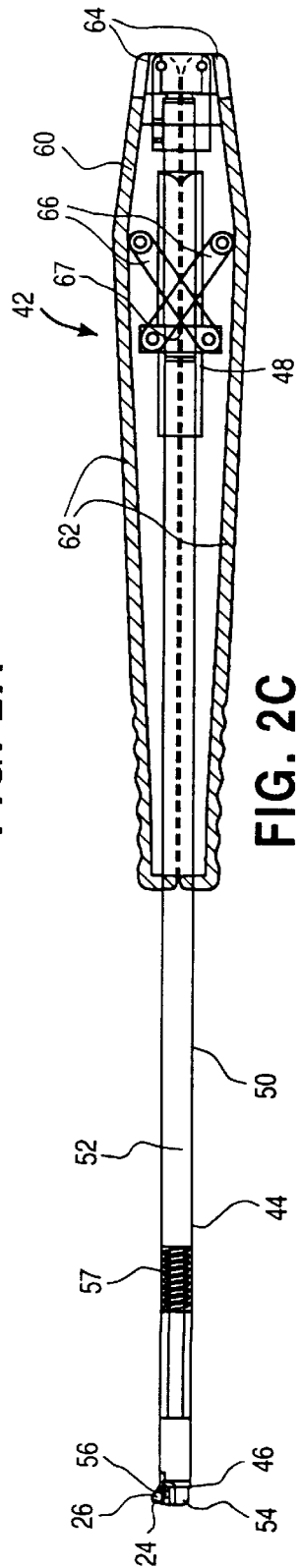

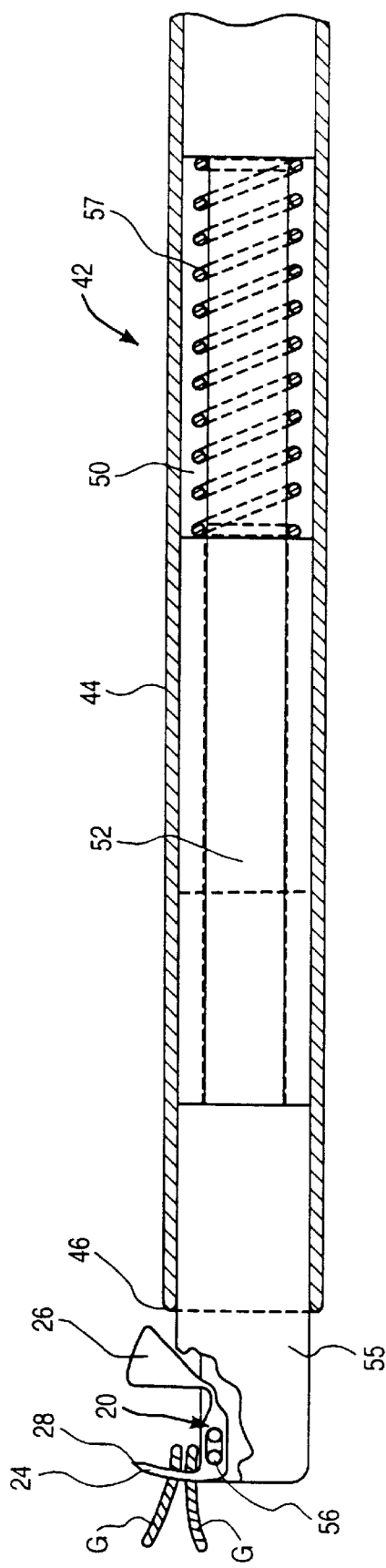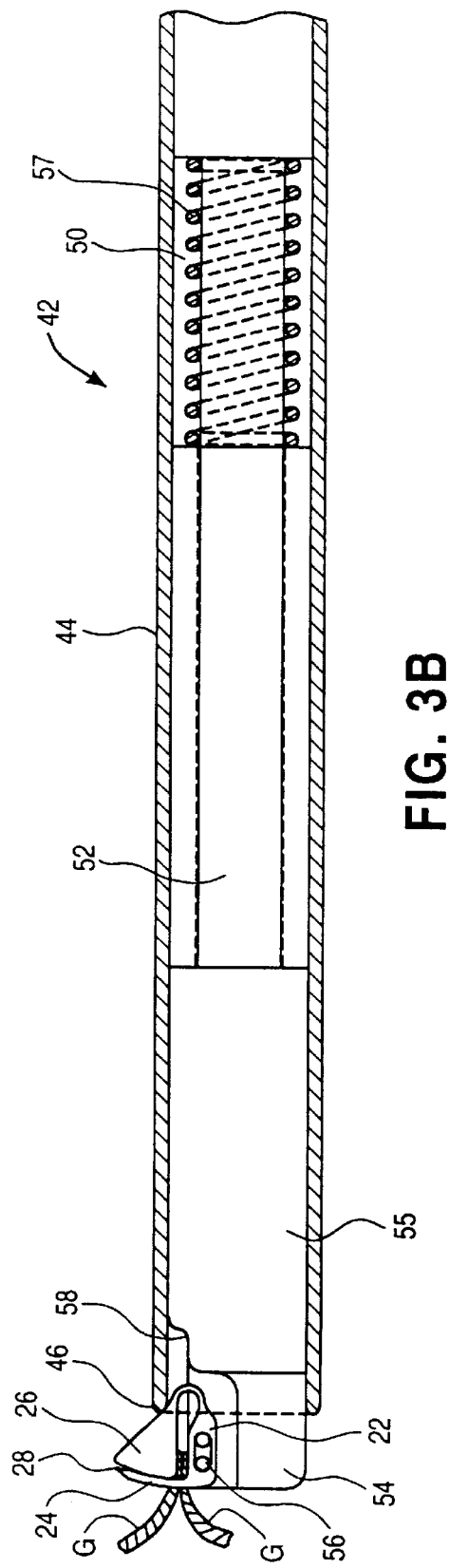
FIG. 3A
FIG. 3B

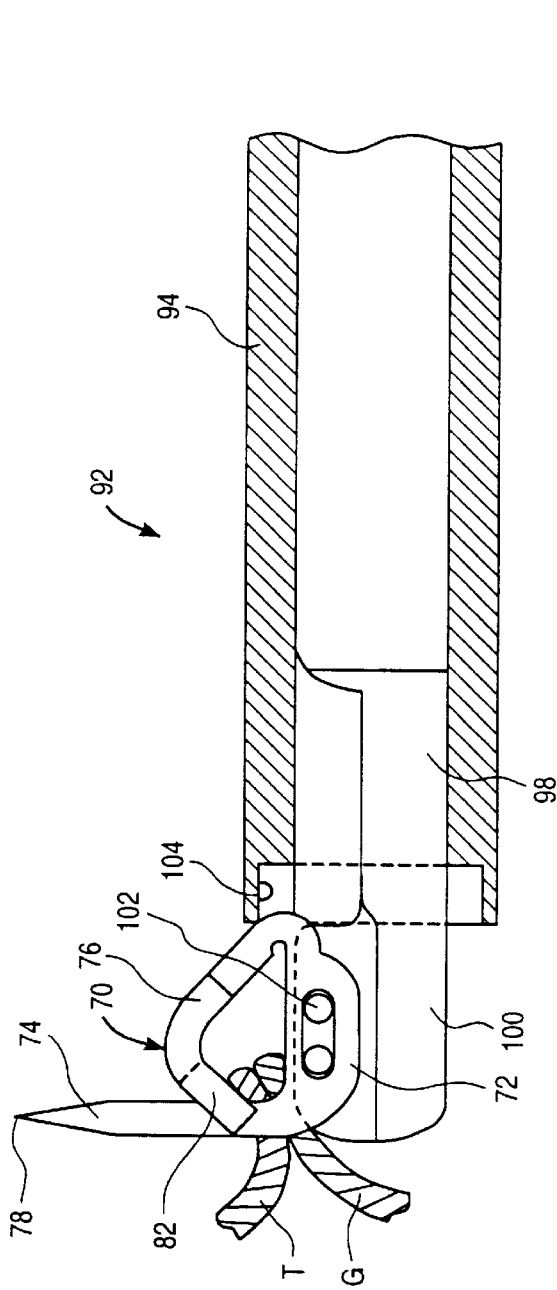
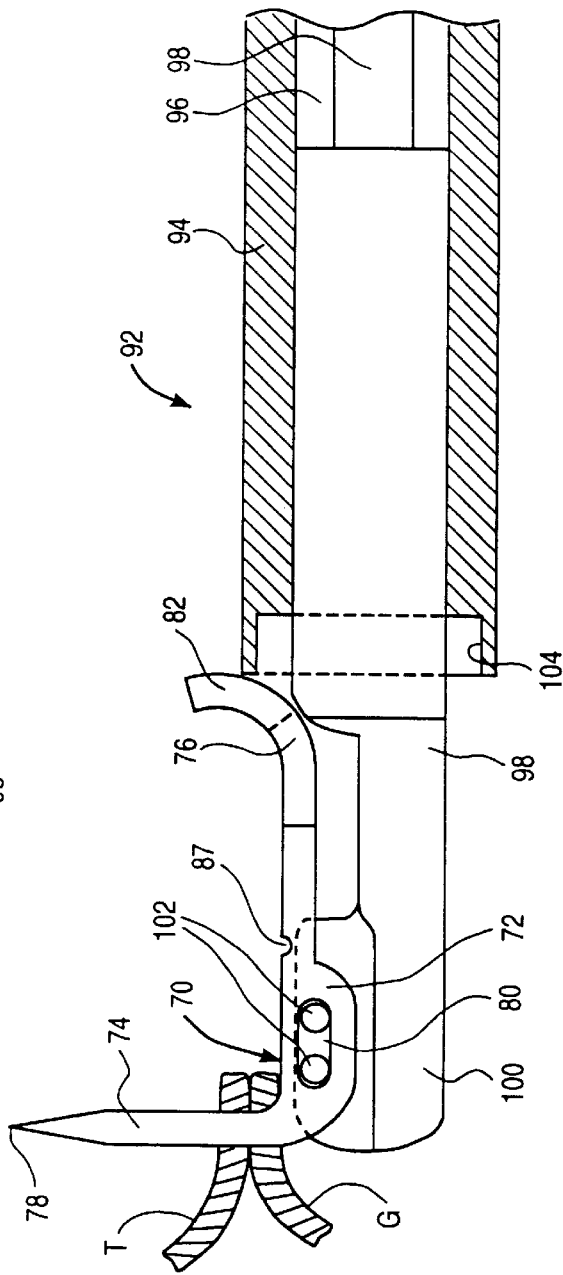
FIG. 6B
FIG. 6A

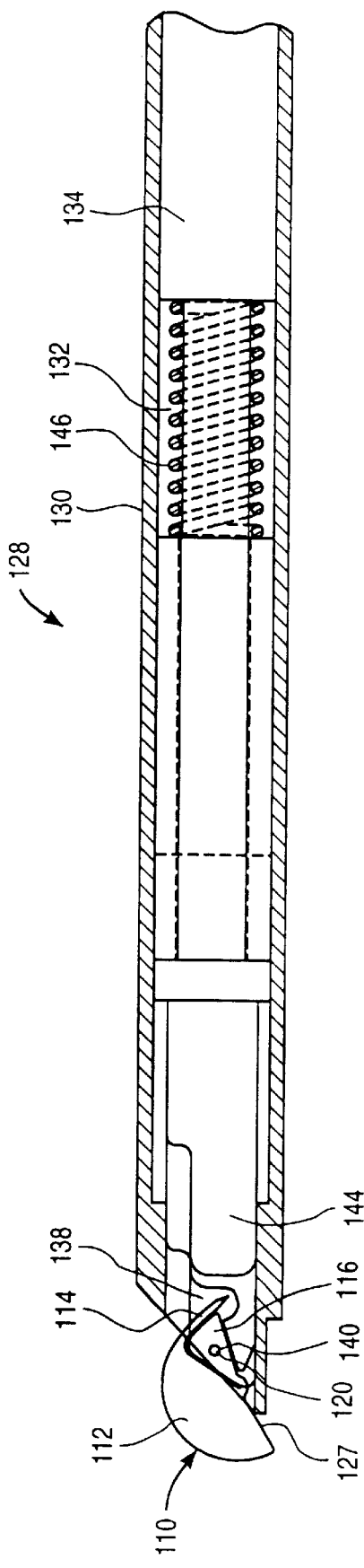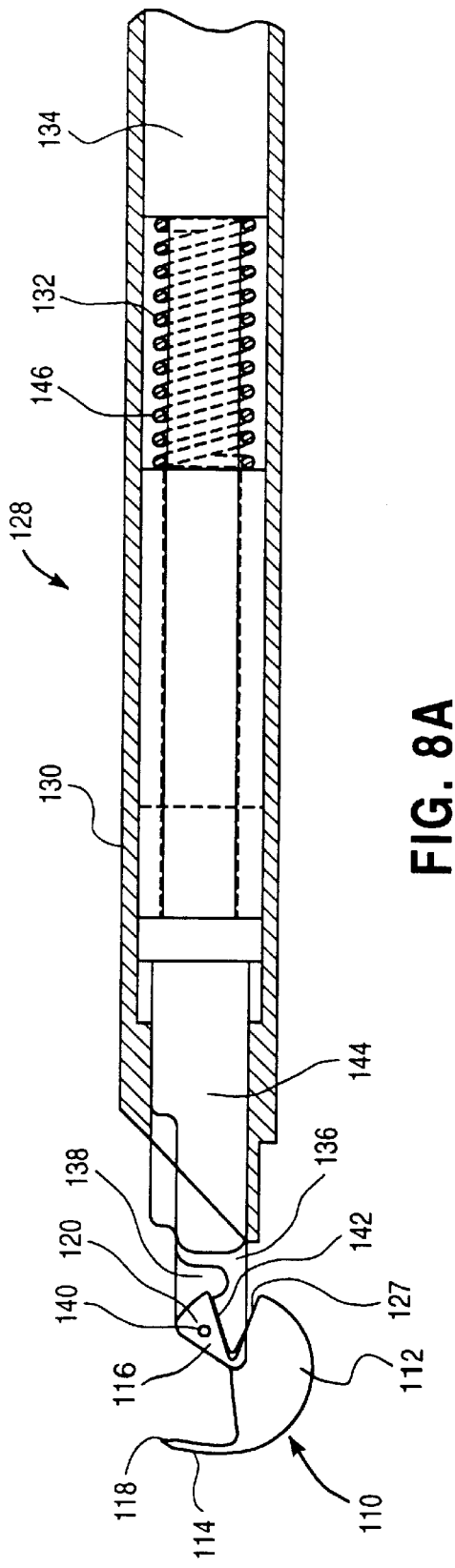
FIG. 8B
FIG. 8A

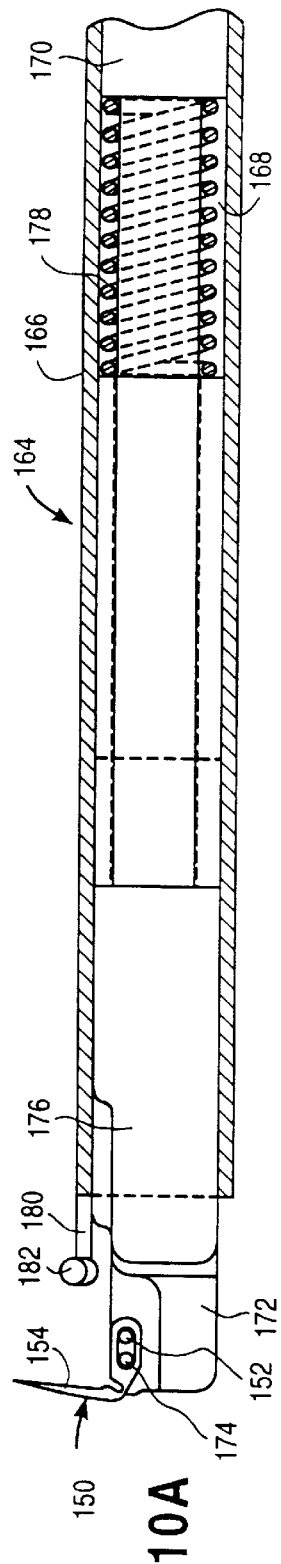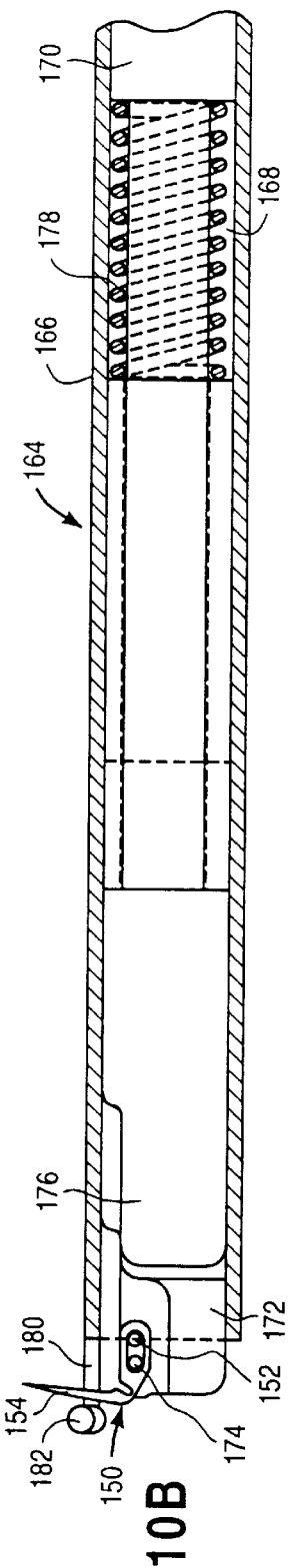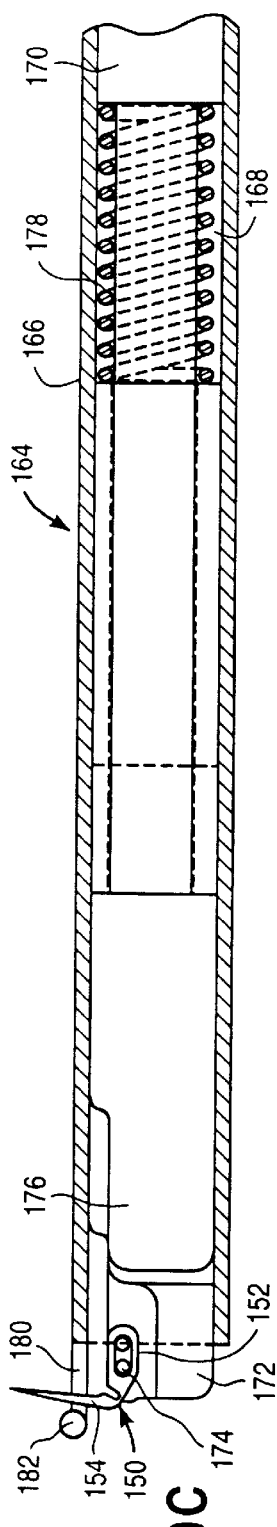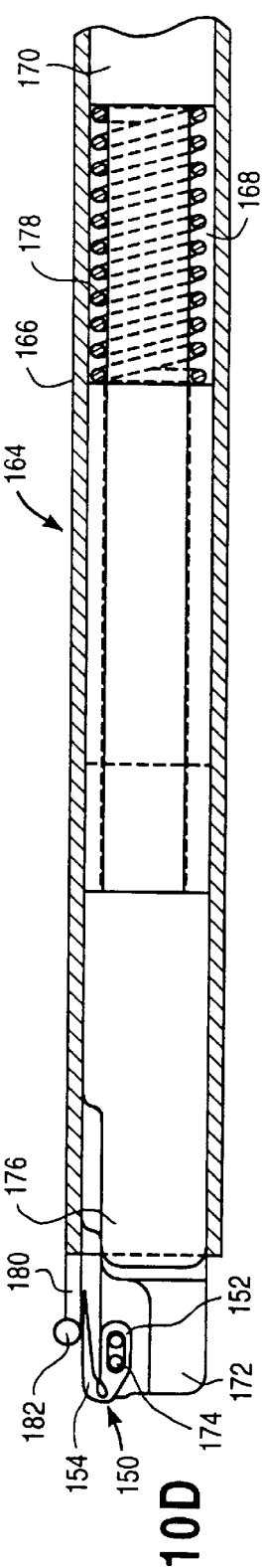

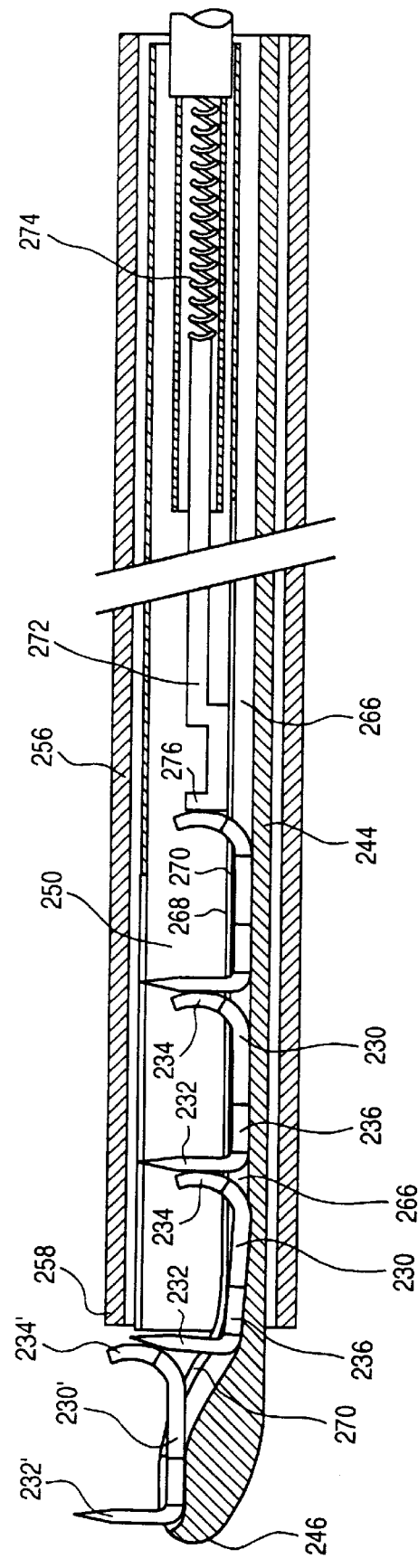
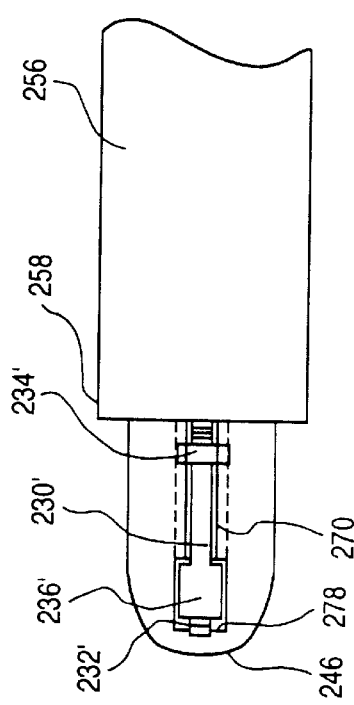
FIG. 15B
FIG. 15C

SURGICAL CLIPS AND METHODS FOR TISSUE APPROXIMATION

CROSS-REFERENCE TO RELATED APPLICATION

This application is a continuation of application Ser. No. 08/598,513, filed Feb. 8, 1996 is now U.S. Pat. No. 5,976, 159, which is a continuation-in-part of copending application Ser. No. 08/394,333, filed Feb. 24, 1995, the complete disclosure of which is hereby incorporated herein by reference for all purposes.

FIELD OF THE INVENTION

The present invention relates generally to surgical instruments and methods, and more specifically to devices and methods for surgical wound closure, tissue approximation and attachment, and vascular anastomosis, especially coronary artery anastomosis.

BACKGROUND OF THE INVENTION

In coronary artery disease, one or more of the coronary arteries which supply oxygenated blood to the heart are partially or entirely blocked by a build-up of atherosclerotic plaque within the artery. This deprives the heart muscle of oxygen and nutrients, leading to myocardial infarction and even death.

Coronary artery bypass grafting remains the gold standard for the surgical treatment of severe coronary artery disease. In coronary artery bypass grafting, or CABG, a graft vessel is used to bypass a blockage in a coronary artery by connecting the distal end of the graft vessel to the coronary artery downstream of the blockage and connecting the proximal end of the graft vessel to a source of arterial blood upstream of the blockage. Various types of graft vessels may be used, including a saphenous vein taken from the patient's leg, a radial artery removed from the patient's forearm, or a prosthetic graft made of expanded polytetrafluoroethylene, Dacron, or other suitable material. Additionally, the left or right internal mammary arteries, which originate from the subclavian artery and reside on the top of the chest wall, may be resected at a distal location and left intact proximally, the free distal end then being connected to the diseased coronary artery downstream of the blockage. Similarly, the gastroepiploic artery, which originates from the gastroduodenal artery in the abdomen, may be resected at a distal location in the abdomen and passed into the thorax through a puncture in the diaphragm for attachment to the diseased coronary artery. Other types of graft vessels may also be used, as well as combinations of several different types of graft vessels in order to bypass multiple coronary blockages.

The surgical interconnection of two vascular structures, such as a graft vessel and a coronary artery, is a process known as anastomosis. In CABG, the anastomosis of a graft vessel to a coronary artery is particularly challenging. Several factors contribute to this challenge. First, the scale of the vessels is extremely small, the coronary arteries having a diameter on the order of about 1–5 mm, and the graft vessels having a diameter on the order of about 1–4 mm for an arterial graft such as a mammary artery, or about 4–8 mm for a vein graft. In addition, the completed anastomosis must not only provide a sealed connection and a patent blood flow path between the graft vessel and the coronary artery, but must further provide a connection which minimizes the exposure of the blood to foreign material or external vessel surfaces which can cause thrombosis at the anastomosis site. Moreover, recent studies suggests that the anastomosis site should not be dramatically different in compliance relative to either the coronary artery or the vascular graft, since such a "compliance mismatch" may also cause thrombus to form at the anastomosis.

Suturing is the technique of choice for coronary anastomosis in the vast majority of CABG cases today. The anastomosis is performed by creating a small opening, or arteriotomy, in the coronary artery, and passing a series of running stitches through the walls of the graft vessel and the coronary artery, respectively, around the perimeter of the arteriotomy so as to compress the end of the graft vessel against the side wall of the coronary artery. The surgeon has a great deal of flexibility in selecting the optimum location for each stitch, based on the shape, structure and condition of the two vessels. The suture needle may be placed initially through the graft vessel wall, and, before the two vessels are closely approximated, the needle then independently placed through the desired location in the target vessel wall. The suture is then tensioned to approximate the two vessels and create a tight, hemostatic seal. The sutured anastomosis thus offers a secure, sealed and patent connection between the two vessels, while having a substantial degree of compliance due to the flexible nature of the suture material.

A drawback of the sutured anastomosis is, however, the high degree of skill, dexterity, and acute visualization required. In addition, the completion of the anastomosis takes a significant amount of time, during which the patient is maintained under cardioplegic arrest and cardiopulmonary bypass. The period of cardioplegic arrest should generally be minimized in order to minimize damage to the heart muscle. Further, in recent years, some attempts have been made at reducing the invasiveness and trauma of CABG surgery by working through smaller incisions or "ports" between the ribs and using endoscopic surgical techniques. Performing microvascular anastomoses with conventional sutures is extremely difficulty when working through small ports, particularly if direct vision of the anastomosis site is not possible and reliance upon endoscopic visualization techniques is necessitated.

Various ideas have been proposed for simplifying and accelerating the process of coronary anastomosis using sutureless anastomosis devices. For example, in U.S. Pat. No. 4,350,160 to Kolesov et al., a device is disclosed for creating an end-to-end anastomosis by everting each vessel end over a split bushing and driving a plurality of staples through the everted vessel ends. For coronary anastomosis, this device requires that the coronary artery be severed downstream of the blockage and the downstream end dissected away from the surface of the heart in order to allow it to be connected end-to-end to the graft vessel. This adds an undesirable increase in time, difficulty and risk to the procedure. In addition, the staples in the Kolesov device are always positioned in a fixed pattern, allowing no flexibility in selecting the location in which each staple is to be driven through the vessels.

In U.S. Pat. No. 4,624,257 to Berggren et al., a device is disclosed for creating either end-to-end or end-to-side anastomoses. The device consists of a pair of rigid rings each having a central opening through which the end of the coronary or graft vessel may be drawn through and everted over the ring. A set of sharp pins extend outwardly from the face of each ring and pierce through the vessel wall to maintain the vessel in the everted configuration. The rings are then joined together to align the end of the graft vessel with the opening in the target vessel. While this device may be suitable for end-to-side anastomosis, eliminating the need to sever and isolate a free end of the coronary artery, the device requires that the side wall of the coronary artery be everted through the central opening of the ring, a maneuver which is likely to be extremely difficult in coronary anastomosis due to the structure and size of the coronary arteries. Moreover, the use of rigid rings that completely encircle the graft vessel and the arteriotomy creates a severe compliance mismatch at the anastomosis site which could lead to thrombosis.

An additional device which has been proposed for end-to-side anastomosis is seen in U.S. Pat. No. 5,234,447 to Kaster et al. This device consists of a rigid ring having a plurality of pointed legs extending from the ring axially in the distal direction and a plurality of angled legs extending axially from the ring in the proximal direction. The graft vessel is placed through the middle of the ring and the end is everted over the pointed legs, which puncture the vessel wall and retain it on the ring. The pointed legs are then bent outwardly, and the everted end of the graft vessel and the outwardly-oriented pointed legs are inserted through an arteriotomy in the target vessel so that the pointed legs engage the interior wall of the target vessel. The angled legs on the proximal end of the ring are then bent toward the target vessel to penetrate the outer wall thereof. While the Kaster device has a simple one-piece design and avoids the need to evert the wall of the target vessel over the device as proposed in Berggren, the device maintains a rigid ring structure which results in inadequate compliance at the anastomosis. In addition, the rigidity of Kaster's device leaves the surgeon little flexibility in selecting the optimum location where each leg of the device should be driven into the graft and target vessels, in contrast to the flexibility available when placing suture stitches.

U.S. Pat. No. 4,586,503 to Kirsch et al. discloses an alternative scheme for creating microvascular anastomoses. The Kirsch device consists of a plurality of individual clips each consisting of a pair of arcuate legs interconnected by a bridging section. The edges of the vascular tissue to be anastomosed are approximated and everted outwardly so that a clip can be placed over the tissue edges, and the clip is then crimped to permanently deform the legs in an inward position. The clip thereby retains the edges of the tissue together without puncturing the tissue. A plurality of clips are placed around the graft vessel in this manner to accomplish the anastomosis. The Kirsch device eliminates the compliance problems of rigid ring-type devices, and allows the surgeon the flexibility to select the optimum location for the placement of each clip. However, the Kirsch clips suffer from several disadvantages. For example, placement of the clips while maintaining eversion and approximation of the tissue edges is difficult and time-consuming. Typically, two pairs of forceps are needed to hold the tissue edges in approximation while a third hand applies the clip, in contrast to suturing, where only one tissue edge needs to be held at one time while the suture needle is driven through it. The Kirsch clips are especially awkward in endoscopic applications, where access, visualization, and maneuverability of instruments are limited. Moreover, in end-to-side anastomosis, the tissue edges along the arteriotomy must be everted outwardly and approximated with the everted end of the graft vessel, a maneuver which becomes increasingly difficult as the ends of the arteriotomy are approached. In addition, due to variation in vessel size and structure, variation in the crimping force applied, and other factors, the clips may not reliably maintain the anastomotic connection.

In view of the foregoing, devices and methods are needed which facilitate the performance of vascular anastomosis, especially coronary anastomosis, but which eliminate the various drawbacks of prior devices. The devices and methods should allow the surgeon to select the specific locations on the graft and target vessels where the device is to be applied, similar to selecting the location of each stitch in a sutured anastomosis. The devices and methods should be relatively simple to utilize without requiring an undue degree of skill and dexterity, even at the small scale of the coronary arteries, and even in endoscopic applications. The devices and methods should be useful for performing end-to-side, end-to-end and side-to-side anastomoses. Further, the devices and methods should produce an anastomosis which is reliably sealed and patent, with a degree of compliance comparable to sutured anastomosis.

SUMMARY OF THE INVENTION

The invention provides surgical clips and methods that meet the foregoing needs, and that are useful not only for coronary anastomosis, but for anastomosis of a variety of other vascular structures, as well as in ligation, wound closure and other tissue approximation and attachment applications. The invention offers a simple and convenient solution to coronary anastomosis, allowing the anastomosis to be performed using only two hands more quickly and easily than existing devices, but with the hemostasis, patency, compliance and reliability of sutures. The devices and methods of the invention are useful not only in conventional open surgical procedures, but in endoscopic, laparoscopic, thoracoscopic and other minimally-invasive procedures as well.

In a first embodiment of the invention, a surgical clip is provided for approximating or attaching a first tissue layer to a second tissue layer. The first and second tissue layers may be any of various tissue structures, such as flaps of tissue adjacent to a wound or incision in a vessel, organ or body wall, but the invention is particularly suitable for vascular anastomosis, wherein a graft vessel is joined to a target vessel. The graft vessel has a free end and a graft vessel wall defining a graft lumen. The target vessel has a target vessel wall defining a target lumen and has an opening in the target vessel wall, which may be an incision or other opening formed in the target vessel wall (for end-to-side or side-to-side anastomoses), or an opening at a free end of the target vessel (for end-to-end anastomoses). The surgical clip includes a clip body having a distal extremity with a distal end and a proximal extremity with a proximal end. The distal end is configured to penetrate through the graft vessel wall near the free end and through the target vessel wall near the opening such that both the distal and proximal ends of the clip body are outside the graft and target vessels. At least a portion of the clip body is shapable so as to compress the graft vessel wall against the target vessel wall with the target vessel lumen in communication with the graft vessel lumen.

By penetrating the graft and target vessel walls, the surgical clip provides the long-term reliability of a sutured connection. In addition, maintaining both ends of the clip outside of both the graft and target vessels minimizes the amount of foreign material contacting blood, eliminates the need for an internal anvil which must be removed after clip application, facilitates visual confirmation of successful application of the clip, and permits manipulation of the ends of the clip to re-apply, reposition or remove the clip. Further, the surgical clip provides a reliable hemostatic seal by having a deformable portion which compresses the graft vessel wall against the target vessel wall. Moreover, through the use of a plurality of individual surgical clips, the invention provides the surgeon with the flexibility to select the ideal location on both the target and graft vessel walls to which each clip should be applied, depending upon vessel structure, condition and shape. The use of multiple independent clips also produces an anastomotic connection having compliance comparable to a sutured anastomosis.

The surgical clip may have a variety of configurations. The clip body will generally have an outer surface against which the graft and target vessel walls are compressed. In one embodiment, the proximal extremity comprises a leg extending from the clip body that is movable between an open position spaced apart from the distal extremity and a closed position closer to the distal extremity. The proximal extremity has an inner surface which faces the outer surface of the clip body in the closed position. The clip body is thus "shaped" by moving the proximal extremity into the closed position, thereby compressing the graft and target vessel walls between the inner and outer surfaces. The proximal extremity may be hingedly coupled to the clip body to facilitate movement thereof, but is preferably configured to be inelastically deformed from the open into the closed position.

The movable proximal extremity may also be configured to contact or to extend across the distal extremity in the closed position. In one configuration, the proximal extremity has an end portion which includes two generally parallel segments which extend across the distal extremity in the closed position and a slot between the parallel segments for receiving the distal extremity. The proximal extremity may also be configured to shield the distal end of the distal extremity in the closed position to prevent inadvertent injury to tissue. Preferably, the proximal extremity is configured to prevent its passage through the graft and target vessel walls. For example, the proximal extremity may have a cross-sectional area which is substantially larger than that of the distal extremity so that it cannot pass through the puncture created by the distal extremity. The proximal extremity may also be oriented at an angle, usually at least about 90° relative to the distal extremity to inhibit its passage through the vessel walls.

In another embodiment, the distal extremity is movable between an open position spaced apart from the proximal extremity and a closed position closer to the proximal extremity, and the distal extremity has an inner surface which compresses the graft and target vessel walls against the outer surface of the clip body in the closed position. Preferably, the distal extremity is inelastically deformable into the closed position.

The distal extremity is preferably oriented such that its inner surface is at an angle of at most about 90° relative to the outer surface of the clip body. The inner surface (or the entire distal extremity) may also be arcuate in shape. The distal extremity is usually tapered to a sharp point at its distal end to facilitate penetration of the graft and target vessel walls. One or more barbs may be provided near the distal end to maintain the graft and target vessel walls on the distal extremity.

The invention also provides an applier for applying the surgical clip. The applier includes a holding mechanism for releasably holding a surgical clip and a shaping mechanism for shaping the clip so as to compress the graft vessel wall against the target vessel wall. Although a variety of holding mechanisms are possible, in one embodiment the holding mechanism comprises a pin at the distal end of the applier, in which case the surgical clip includes a middle portion having an aperture for receiving the pin. Various types of shaping mechanisms are also possible, but in an exemplary configuration, the clip applier includes an inner shaft and an outer shaft axially movable with respect to each other. The clip is held by a first of the inner and outer shafts, and the clip body is shaped by engagement with a second of the inner and outer shafts. In a particularly preferred aspect, the clip applier is configured for endoscopic, laparaoscopic, thoracoscopic, or other minimally-invasive procedures, by holding the clip at the end of a small-profile elongated shaft suitable for positioning through a small incision, trocar sleeve, tubular port, cannula or the like. An actuator at the proximal end of the shaft permits remote application of the clip from outside the body cavity.

In another embodiment, the surgical clip of the invention comprises a clip body, a needle portion extending from the clip body that has a distal end configured to penetrated the graft and target vessel walls and to extend outside of the graft and target vessels. The clip body is configured to prevent its passage through the graft and target vessel walls so that it remains outside of the graft and target vessels. A retainer is further provided on the clip for retaining the graft and target vessel walls on the needle portion.

In one configuration, the retainer comprises a leg attached to the clip body and movable from an open position spaced apart from the needle portion to a closed position closer to the needle portion. The leg may be hingedly movable or inelastically deformable into the closed position. Preferably, the retainer is configured to compress the graft vessel wall against the target vessel wall for reliable hemostasis. The leg may also be configured to shield the distal end of the needle portion in the closed position.

Alternatively, the retainer may comprise a barb or other retention device on the needle portion itself. A plurality of barbs may be provided at spaced apart positions along the extremity of the needle portion so that the needle portion may be passed through the graft and target vessel walls a desired amount and the barbs will prevent the needle portion from backing out of the vessel walls. As an alternative to barbs, a retainer which is unidirectionally slidable or threadable onto the needle portion may be provided which is placed on the needle portion after it has been passed through the graft and target vessel walls. The needle portion is preferably hook-shaped, J-shaped or oriented at an angle of at least about 90° relative to the clip body so that the needle portion may be advanced through the vessel walls until its curved portion or the clip body engages the vessel wall. The barbs or other retaining devices are positioned relative to the clip body so as to maintain the graft vessel wall in compression against the target vessel wall.

In an additional embodiment, the surgical clips of the invention are configured to be coupled to a flexible ring-shaped band, which is preferably a continuous ring of suture, metal or plastic wire or strip, or other flexible material. The band defines a central opening through which the graft vessel may be received. Each clip has a first portion for engaging the graft vessel wall, and a second portion for engaging the target vessel wall, the first and second portions being configured to retain the graft vessel wall in sealing engagement with the target vessel wall. A plurality of clips are positionable at spaced-apart locations around the band. In this way, application of the clips to the vessels is accomplished by simply placing the band over the end of the graft vessel and applying each clip to the vessel wall. The graft vessel may then be positioned adjacent to the opening in the target vessel and each clip applied to the target vessel wall to create a sealed anastomotic connection. The band may be either left in place, or configured for removal by cutting or otherwise detaching the ring from the clips.

Preferably, the clips are coupled to the band so as to be slidable to the desired position around the perimeter of the band. In one configuration, the clips have a loop or eyelet through which the band may be slidably received. The clips in this embodiment may have any of various configurations suitable for vascular anastomosis, including those described above, as well as other configurations not specifically described.

In a preferred embodiment, a method of joining a graft vessel to a target vessel according to the invention comprises providing a plurality of surgical clips each including a clip body having a distal extremity with a distal end and a proximal extremity with a proximal end; penetrating the graft vessel wall and the target vessel wall with the distal extremity of each surgical clip such that the distal and proximal ends are disposed outside of the graft and target vessels; and shaping a portion of each clip body outside of the graft and target vessels so as to compress the graft vessel wall against the target vessel wall with the graft lumen in communication with the target lumen. In this way, a robust, reliable and hemostatic anastomosis is provided which is simple and convenient to perform using only two hands, which minimizes the amount of foreign material in contact with the blood stream, which allows the surgeon to place each clip in the optimum location based on the size, shape and condition of the vessels, and which provides a degree of compliance in the completed anastomosis comparable to that of sutured anastomoses. The invention thus combines the ease of application, flexibility of position, reliability, and compliance of sutures, with the convenience and quickness of surgical clips.

Because of its simplicity and convenience, the invention is particularly well-adapted for use in endoscopic, laparoscopic, thoracoscopic and other minimally-invasive applications. The clips may be applied to a body structure using slender instruments positioned through percutaneous ports such as trocar sleeves, tubular cannulas, or small incisions, under direct visualization through such ports or under video-based visualization by means of an endoscope positioned through a port.

The nature and advantages of the invention will become more apparent from the following detailed description taken in conjunction with the accompanying drawings.

BRIEF DESCRIPTION OF THE DRAWINGS

FIGS. 2A and 2B are front and top cross-sectional views, respectively, of a clip applier for applying the surgical clip of FIGS. 1A–1B in an open position.

FIG. 2C is a front cross-sectional view of the clip applier of FIG. 2A in a closed position.

FIGS. 3A–3B are side cross-sectional views of a distal portion of the clip applier of FIGS. 2A–2C in open and closed positions, respectively, illustrating the application of the surgical clip to two portions of tissue.

FIGS. 6A–6B are side cross-sectional views of a distal portion of a clip applier in open and closed positions, respectively, illustrating the application of the surgical clip of FIGS. 5A–5C to two portions of tissue.

FIGS. 8A–8B are side cross-sectional views of a distal portion of a clip applier in open and closed positions, respectively, illustrating the application of the surgical clip of FIGS. 7A–7B to two portions of tissue.

FIGS. 10A–10D are side cross-sectional views of a distal portion of a clip applier in four successive configurations, illustrating the closure of the surgical clip of FIGS. 9A–9B.

FIGS. 15B–15C are side cross-sectional and top views, respectively, of a distal portion of the clip applier of FIG. 15A.

DETAILED DESCRIPTION OF SPECIFIC EMBODIMENTS

Figure 1A:
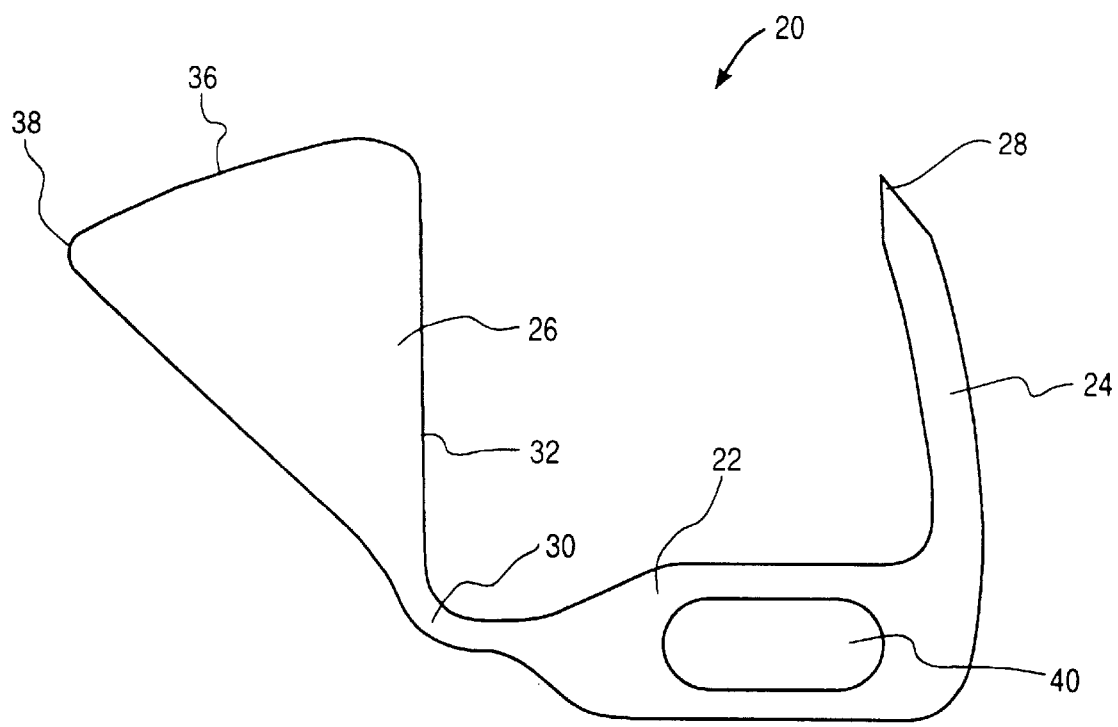
FIGS. 1A–1B are front elevational views of a surgical clip constructed in accordance with the principles of the invention in an open and a closed position, respectively.
Figure 1B:
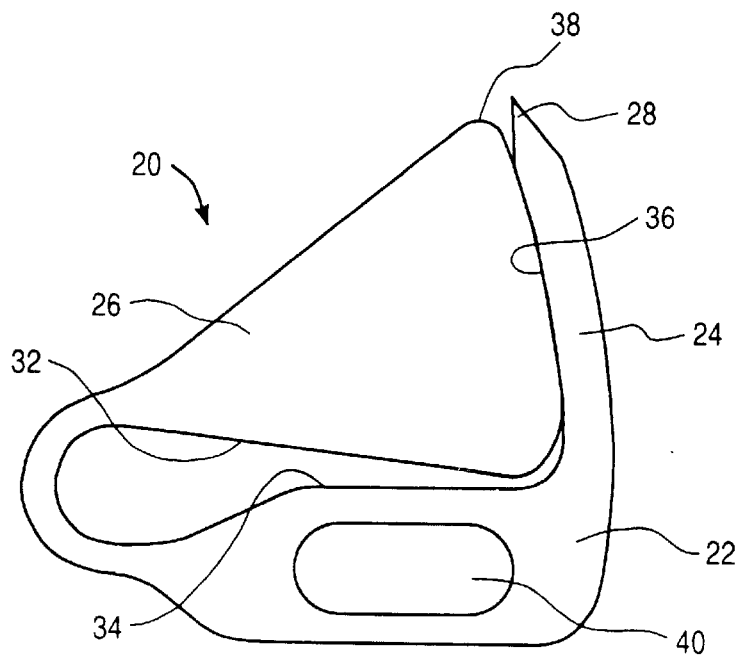

A first embodiment of a surgical clip according to the invention is illustrated in FIGS. 1A–1B. Surgical clip 20 comprises a clip body 22, a distal extremity 24 attached to a first end of clip body 22 and a proximal extremity 26 attached to a second end of clip body 22. Distal extremity 24 has a sharp distal point 28 configured to penetrate one or more layers of tissue such as a wall of a vessel, and is sufficiently rigid to allow the distal extremity to be driven through such tissue without bending or buckling. Distal extremity 24 may be straight, angled, or arcuate, and may include barbs or other means of retention, as further described below. The distal extremity will have a length sufficient to pass through the combined thickness of all tissue layers to be fastened together using clip 20, preferably about twice the combined thickness of the tissue layers, e.g. about 2–5 mm for coronary anastomosis applications, or larger for application to thicker tissues such as the aorta, heart wall, intestines, bowel, or fascia.

Proximal extremity 26 is movable between an open position in which it is spaced-apart from distal extremity 24 as shown in FIG. 1A, and a closed position in which it is closer to distal extremity 24, as shown in FIG. 1B. Proximal extremity 26 may be movably attached to clip body 22 in various ways, including by a pivot pin, living hinge or the like, but, in a preferred embodiment, is attached by a deformable leg 30, usually constructed of an inelastically deformable metal so that once it is placed in the closed position, proximal extremity 26 will not return to the open position without similar deformation. If a hinge arrangement is used, a latch (not shown) may be provided on clip body 22 to engage and maintain the proximal extremity in the closed position. Proximal extremity 26 has an inner surface 32 which faces an outer surface 34 of clip body 22 in the closed position. In the open position, inner surface 32 is disposed sufficiently apart from outer surface 34 to facilitate placement of distal extremity 24 through the tissue layers without interference, usually being at an angle of at least about 45°, usually about 60°–120°, and preferably about 90°, relative to outer surface 34. In the open position, clip 20 thus forms a general C-shape or U-shape, with a gap between the distal and proximal extremities. The size of the gap will depend upon the size and nature of the tissue to which clip 20 is to be applied, with the distance between distal extremity 24 and proximal extremity 26 usually ranging from about 0.5–8.0 mm, more particularly about 1.0–5.0 mm, and preferably, in coronary applications, about 1.5–3.0 mm.

In the closed position, inner surface 32 is preferably separated from outer surface 34 by a distance of less than about the combined thickness of the tissue layers to be fastened together with clip 20. In this way, the tissue layers will be compressed against one another between proximal extremity 26 and clip body 22, providing important advantages, as described in more detail below. The amount of tissue compression will depend upon the nature of the tissue, the need for a fluid seal, the internal pressures of any fluid within the tissue, and other factors, but will usually compress the tissue layers so as to reduce their combined thickness by at least about 10%, and preferably about 30%–50% from their combined, uncompressed thickness. In an exemplary embodiment suitable for coronary anastomosis, inner surface 32 is separated from outer surface 34 by a distance of no more than about 0.02–1.0 mm, and preferably 0.05–0.3 mm, at the closest point between the two surfaces which contact the tissue layers. In other applications involving thicker tissues this distance will be greater, as needed to apply suitable compressive force to the tissues without unnecessarily cutting, crushing or otherwise damaging the tissues.

Proximal extremity 26 is preferably configured to shield distal point 28 of distal extremity 24 in the closed position to avoid the possibility of the distal point causing inadvertent injury to tissue. In one configuration, proximal extremity 26 has an outer side 36 which has a length generally equal to that of distal extremity 24 so that the upper end 38 of outer side 36 is aligned with distal point 28 in the closed position. Outer side 36 further has a shape selected to match that of distal extremity 24, having an arc generally matching that of the inner side of distal extremity 24 in the embodiment of FIG. 1. In other configurations, proximal extremity 26 may include a slot, channel or aperture along outer side 36 which receives all or a portion distal extremity 24 in the closed position, or a separate sleeve or cap (not illustrated) may be placed over distal point 28.

Clip body 22 includes a means by which clip 20 may be held by a clip applier or other instrument for applying the clip to body tissue. In the embodiment of FIGS. 1A–1B, the clip holding means comprises an aperture 40 which extends through the clip body in a direction generally parallel to the axis of movement of proximal extremity 26. Aperture 40 may have various shapes and may, instead of a single aperture, include two or more separate apertures, depending upon the type of clip applier to be used.

FIGS. 2A–2C illustrate a clip applier 42 suitable for applying surgical clip 20 of FIGS. 1A–1B. Clip applier 42 has an outer shaft 44 having a distal end 46, a proximal end 48, and a lumen 50. An inner shaft 52 is slidably disposed within lumen 50. Inner shaft 52 has a clip holding mechanism 54 at its distal end which includes two transverse pins 56 (better seen in FIGS. 3A–3B) that are received within aperture 40 of clip 20. Clip 20 is held so that distal extremity 24 and proximal extremity 26 extend generally radially outward from the longitudinal axis of inner shaft 52. As shown in the top view of FIG. 2B, a clip cover 55 is slidably mounted within outer shaft 44 parallel to a distal portion of inner shaft 52. A spring 57 disposed around inner shaft 52 within lumen 50 engages a proximal end of clip cover 55 and biases it in a distal direction. In this way, clip cover 55 may be retracted in the proximal direction to place a clip 20 on pins 56 as in FIG. 2A, then returned to the distal position of FIG. 2B so as to retain clip 20 on pins 56 as the clip is applied. Clip cover 55 has a cut-out 58 at its distal end to expose distal extremity 24 of clip 20 to facilitate penetrating tissue with the distal extremity.

An actuator handle 60 includes a pair of leaves 62 having proximal ends 64 pivotally attached to the proximal end of inner shaft 52 so that actuator handle 60 remains a fixed distance from surgical clip 20 whether open or closed. A link 66 is pinned at one end to each leaf 62 and at its other end to a collar 67 attached to the proximal end 48 of outer shaft 44. In this way, pivoting leaves 62 inwardly translates outer shaft 44 distally relative to inner shaft 52 from the open position of FIG. 2A to the closed position of FIG. 2C, thereby closing surgical clip 20. A leaf spring (not shown) engages the inner sides of each leaf 62 to bias the leaves outward into the position of FIG. 2A. Alternatively, a tension or compression spring may be mounted around inner shaft 52 so as to engage the proximal end of outer shaft 44 and bias it proximally.

While clip applier 42 is illustrated in a single-fire design capable of holding only one clip at a time, those of ordinary skill in the art will understand that the clip applier of the invention may be designed to hold multiple clips which can be applied repeatedly without manually reloading a clip into the applier after each application. For example, pins 56 could be configured to allow multiple clips to be stacked in parallel, with outer shaft 44 being designed to engage and close only the outer-most clip in the stack. Alternatively, clips 20 could be lined up serially in an axial channel within outer shaft 44 and a pusher could exert a distal force against the proximal end of the line. The pusher would feed clips 20 one-by-one onto pins 56 or other suitable clip holding means after each clip is closed.

Clip applier 42 preferably is configured for use in thoracoscopic, laparoscopic, or other endoscopic surgical procedures, wherein clip holding mechanism 54 and a distal portion of outer shaft 44 and inner shaft 52 are positioned through a trocar sleeve, cannula, port or small incision in the body wall, preferably between the ribs if operating in the thoracic cavity. The distal portion of the clip applier must therefore have a small profile so as to fit through a small access passage, and a sufficient length to reach the surgical site within the body cavity. In an exemplary embodiment, the outer diameter of outer shaft 44 and the largest transverse dimension of clip holding mechanism 54 are less than about 12 mm, preferably less than about 10 mm, and outer shaft 44 has a length of at least about 10 cm, preferably at least about 20 cm.

FIGS. 3A–3B illustrate a distal portion of clip applier 42 in the open and closed positions, respectively. Two layers G, T of tissue to be fastened together are penetrated with distal point 28 of clip 20 so that the edges of the tissue are disposed within the gap between distal extremity 24 and proximal extremity 24. Actuator handle 60 of clip applier 42 is then actuated by pivoting leaves 62 inwardly, translating outer shaft 44 distally relative to inner shaft 52. Distal end 46 of the outer shaft engages the proximal side of proximal extremity 26 and deforms it into the closed position of FIG. 3B. The edges of tissue layers G, T are thereby compressed between proximal extremity 26 and clip body 22. Leaves 62 contact each other and/or outer shaft 44 in the closed position, preventing translation of outer shaft 44 beyond that necessary to close clip 20 with the desired degree of compression to avoid excessive crushing of tissue layers G,T. This compression of tissue is particularly advantageous when using clip 20 to perform anastomosis of two vessels such as arteries. Such compression not only accelerates the growing together of the two vessels, but creates an immediately hemostatic seal at the anastomosis site.

Figure 4:
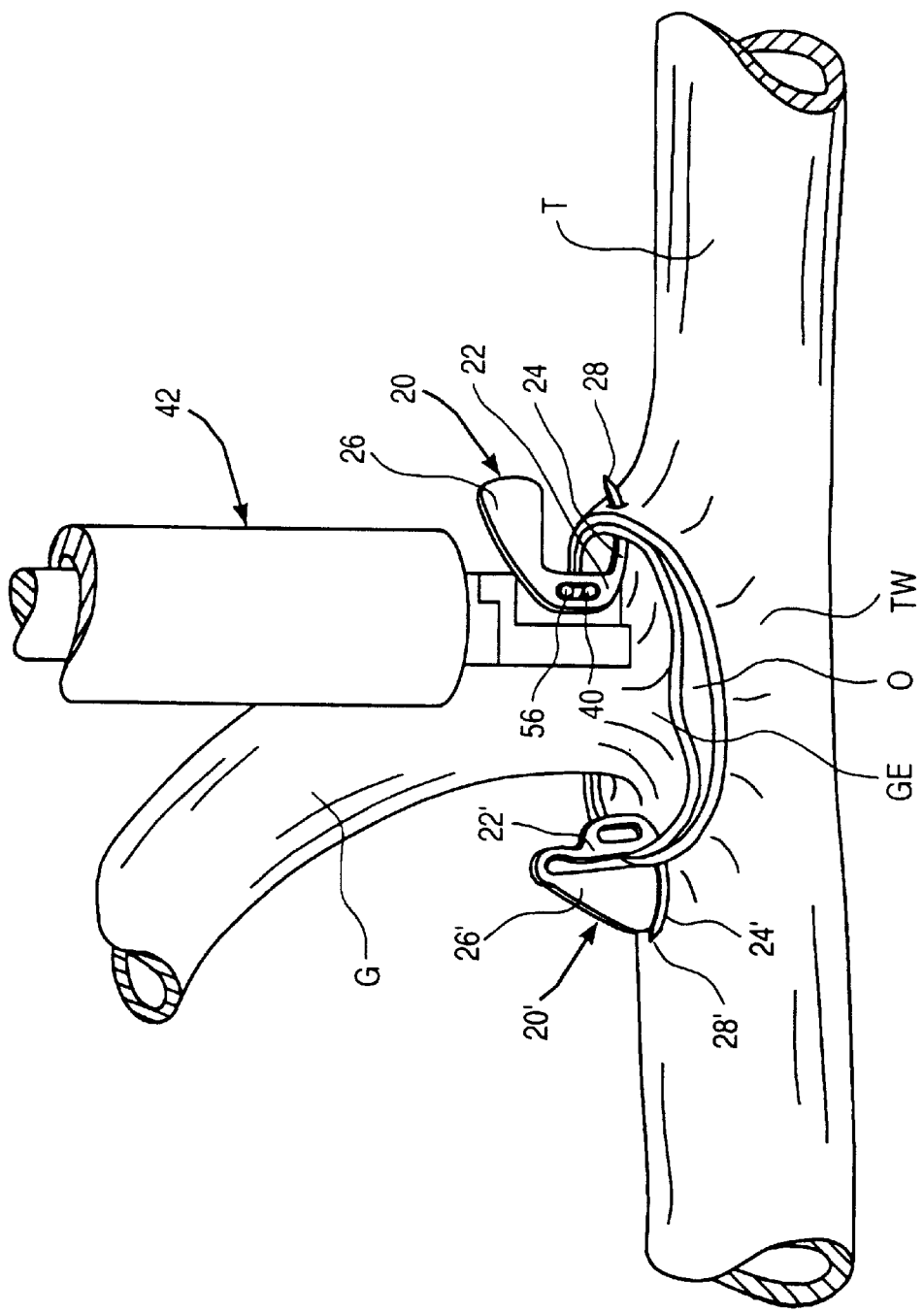
FIG. 4 is a perspective view of a distal portion of the clip applier of FIGS. 2A–2C schematically illustrating the use of the surgical clip in the anastomosis of a graft vessel to a target vessel.

The performance of vascular anastomosis using clip applier 42 and clip 20 is illustrated in FIG. 4, which shows a graft vessel G being anastomosed to a target vessel T. Graft vessel G may be any of a variety of vascular structures, including blood vessels, intestines, bowel and other body ducts. The invention is particularly useful, however, for anastomosis of small blood vessel such as the coronary arteries and the conduits commonly used in coronary artery bypass grafting (CABG), including internal mammary arteries, saphenous vein grafts, radial artery grafts, gastroepiploic arteries, and other natural and artificial vascular grafts. The invention may be used either for "proximal" anastomosis—that is, the connection of the upstream end of a graft to a source of blood such as the aorta—or "distal" anastomosis, the connection of the downstream end of the graft to a coronary artery below a blockage in the artery. Thus, in the context of coronary anastomosis, the term "graft vessel" is used herein to mean the vascular graft used to provide a new conduit to a coronary artery, while "target vessel" is used to mean either the arterial blood source vessel (e.g. aorta) or the coronary artery to which the "graft vessel" is connected. In other applications, "graft vessel" and "target vessel" may simply refer to the two vessels, organs or other structures which are being connected together. In addition, while FIG. 4 illustrates an end-to-side anastomosis as is common in CABG surgery, the clips and appliers of the invention are useful in forming end-to-end and side-to-side anastomoses as well.

As shown in FIG. 4, an end GE of graft vessel G is connected to a side wall TW of target vessel T around an opening O formed in wall TW by a surgical knife, scissors or other suitable instrument. In an artery such as a coronary artery, opening O is known as an arteriotomy. Initially, either inside or outside the body cavity, one or more clips 20 may be attached to graft vessel end GE by puncturing distal point 28 through the graft vessel wall from the exterior side toward the interior side. Usually, this will be done with clip 20 held at the distal end of clip applier 42, which is then positioned adjacent to the opening O in target vessel T. Distal point 28 is then penetrated through target vessel wall TW from the interior of the vessel outward such that the distal edge of graft vessel end GE is approximated with the edge of opening O. This may require slight pursing up of target vessel walls TW around the opening and/or slight flaring or eversion of graft vessel end GE, which is accomplished using surgical forceps or other suitable instruments. Distal extremity 24 is passed through the graft and target vessel walls until clip body 22 is contacting the wall of graft vessel G. Actuator handle 60 of clip applier 42 is then actuated so that outer shaft 44 is advanced distally, deforming proximal extremity 26 into the closed position of clip 20'. Clip applier 42 is then removed by withdrawing pins 56 from aperture 40. A plurality of clips 20, usually at least about 4, preferably 6–30, depending upon vessel size, the need for a fluid seal, the internal pressures in the vessels, and other factors, are applied around the perimeter of opening O in this way until a sealed and secure anastomosis has been achieved.

It may be seen that the graft and target vessel walls are compressed between proximal extremity 26' and clip body 22', providing a secure and hemostatic connection. Distal point 28' is safely shielded by proximal extremity 26' to prevent interference or injury to surrounding tissue. Eventually, graft vessel G and target vessel T will grow together at the anastomosis. However, clips 20, being made of a biocompatible material such as stainless steel, titanium or titanium alloy, tantalum, elgiloy, MP35N, or cobalt chromium-nickel alloy, may be left in the body indefinitely to ensure that the anastomosis remains intact.

Figure 5A:
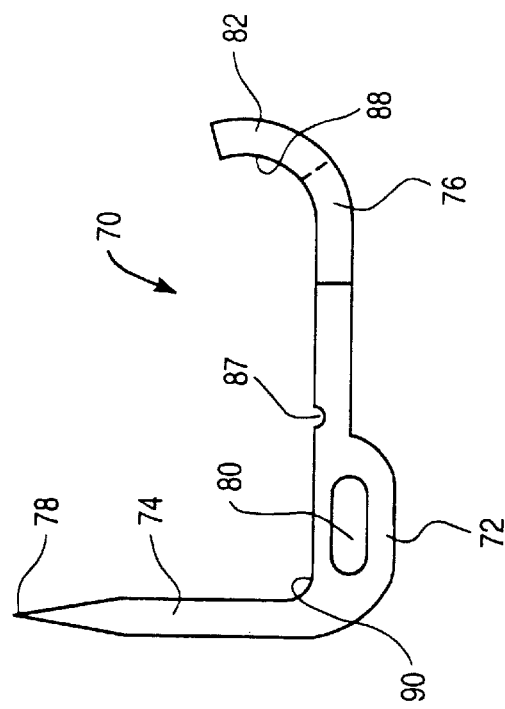
FIGS. 5A and 5C are front elevational views of a second embodiment of a surgical clip constructed in accordance with the principles of the invention in an open and a closed position, respectively.
Figure 5C:
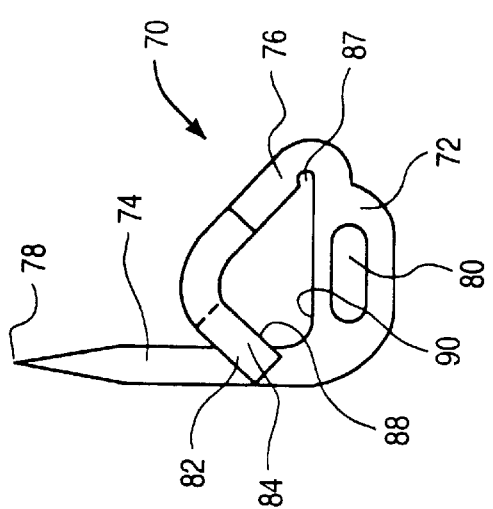
Figure 5B:
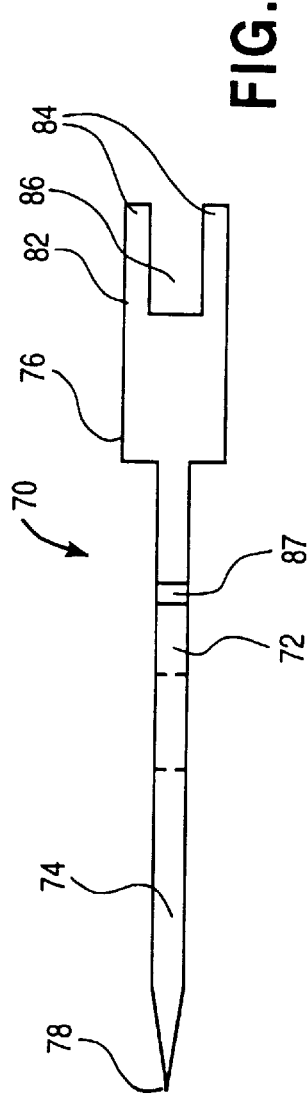
FIG. 5B is a top view of the surgical clip of FIG. 5A in a straightened configuration.

An additional embodiment of a surgical clip according to the invention is illustrated in FIGS. 5A–5C. Surgical clip 70 includes a clip body 72, a distal extremity 74 and a proximal extremity 76. Distal extremity 74 has a sharp distal point 78 adapted to penetrate tissue. Clip body 72 has an aperture 80 for receiving pins 56 on clip applier 42. Proximal extremity 76 has an end portion 82 adapted to overlap or cross-over distal extremity 74 in the closed position shown in FIG. 5C. As illustrated in FIG. 5B, showing a top view of clip 70 in a flattened configuration, end portion 82 has a bifurcated construction with a pair of parallel segments 84 separated by a space 86. Segments 84 are separated by a distance of at least the transverse width (or diameter, if round) of distal extremity 72 to allow distal extremity 74 to be received within space 86 in the closed position of FIG. 5C. Proximal extremity 76 is movable between the open position of FIG. 5A and the closed position of FIG. 5C, preferably being constructed of a biocompatible metal or other deformable material so that the proximal extremity may be inelastically deformed into the closed position. Alternatively, proximal extremity 76 may be hingedly coupled to clip body 72 and end portion 82 may be provided with a catch (not shown) which engages distal extremity 74 in the closed position. Clip 70 may also be constructed of a thermally responsive shape memory alloy such as Nitinol (Raychem Corp.), whereby, once distal extremity 74 has been applied to the target tissue, heat may be applied to clip 70 using heated forceps or other heat-tipped probe (or by heating the distal end of the clip applier itself) so as to raise the proximal extremity to a transition temperature in which it resumes the closed position of FIG. 5C.

In order to facilitate closure of clip 70 in a repeatable and predictable hinge-like manner, a notch 87 may be provided on the inner surface of proximal extremity 76 at the junction of the proximal extremity and clip body 72. When a distally directed force is applied to end portion 82 using clip applier 42 (described below), proximal extremity 76 tends to buckle at notch 87, allowing the proximal extremity to rotate about an axis passing generally through the notch without excessive deformation of the proximal extremity.

Clip 70, as with clip 20 above, is constructed so as to compress the tissue layers to which the clip is applied between proximal extremity 76 and clip body 72. Proximal extremity 76 has an inner surface 88 which faces an outer surface 90 of clip body 72 in the closed position. The clip is preferably configured so that, in the closed position of FIG. 5C, inner surface 88 is separated from outer surface 90 adjacent to distal extremity 74 by a distance of less than the combined thickness of all the tissue layers to which the clip is being applied, preferably about 0.05–0.3 mm for coronary distal anastomosis.

The closure of clip 70 by means of a clip applier 92 is illustrated in FIGS. 6A–6B. Clip applier 92 may be constructed similarly to clip applier 42 of FIGS. 2–3, having an outer shaft 94 with a lumen 96 extending through it, and an inner shaft 98 within lumen 94 over which outer shaft 94 is axially slidable. The proximal portion of the clip applier, not shown in FIGS. 6A–6B, may be constructed like that of clip applier 42, with an actuator handle configured to translate outer shaft 94 distally when actuated. A clip holding mechanism 100 is mounted to the distal end of inner shaft 98, and includes a pair of transverse pins 102 configured to extend through aperture 80 in clip 70. Clip 70 is thus held in an orientation in which distal extremity 74 is disposed transverse to, preferably about orthogonal to, the longitudinal axis of inner shaft 98. A movable clip cover (not shown) like clip cover 55 of FIGS. 2–3 may also be provided at the distal end of inner shaft 98 to retain clip 70 on pins 102. Proximal extremity 76 is disposed so that the curved outer surface of its end portion 82 is engaged by the distal end of outer shaft 94 when the outer shaft is advanced distally. The distal end of outer shaft 94 may be shaped so as to smoothly and completely deform proximal extremity 76 into the closed position of FIG. 6B, including, for example, an annular undercut 104.

In use, a clip 70 is placed on pins 102 and the clip cover is allowed to slide distally over clip body 72 to retain it on the applier. Distal point 78 on clip 70 is penetrated through the tissue layers T, G to which the clip is to be applied as shown in FIG. 6A. The actuator handle is then actuated, advancing outer shaft 94 distally over inner shaft 98 to engage end portion 82 of clip 70 and deform it into the closed position shown in FIG. 6B. The bifurcated end of end portion 82 crosses over distal extremity 78, completely enclosing tissue layers T, G. Advantageously, tissue layers T, G. are compressed between end portion 82 and clip body 72, creating a secure and fluid-tight connection.

Figure 7B:
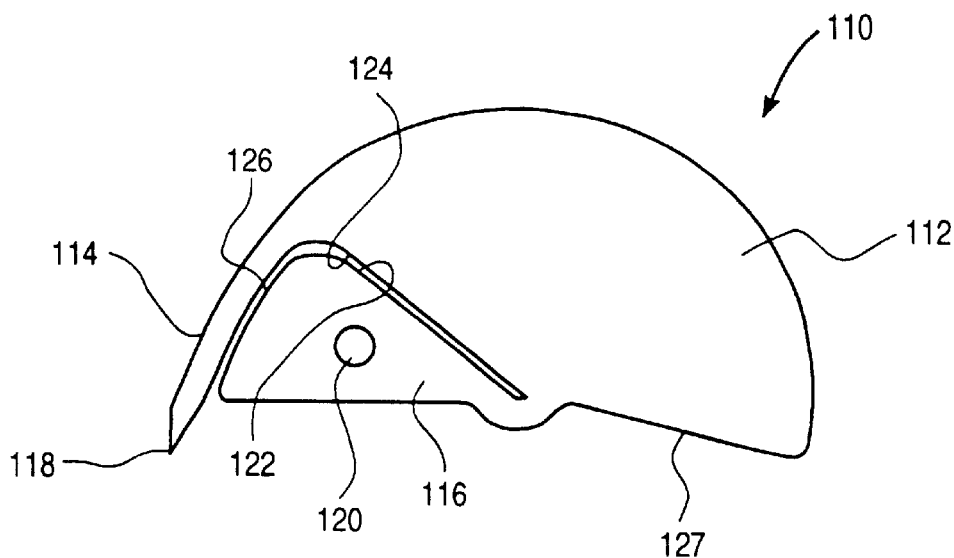
FIGS. 7A–7B are front elevational views of a third embodiment of a surgical clip constructed in accordance with the principles of the invention in an open and a closed position, respectively.
Figure 7A:
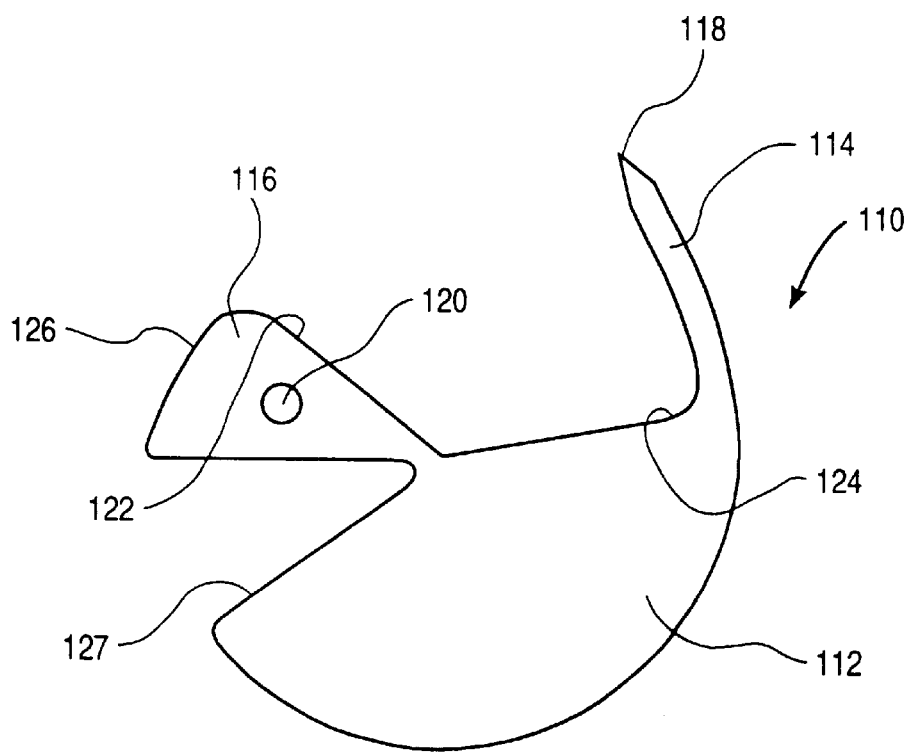

FIGS. 7A–7B illustrate an additional embodiment of a surgical clip according to the invention. Clip 110 includes a clip body 112, a distal extremity 114 and a proximal extremity 116. As in previous embodiments, distal extension 114 has a sharp distal point 118 configured to penetrate tissue. Proximal extremity 116 has an aperture 120 which facilitates holding the clip in a clip applier as described below. Proximal extremity 116 is movable relative to clip body 112 between an open position spaced apart from distal extremity 114 and a closed position closer to distal extremity 114, shown in FIG. 7B. Preferably, the proximal extremity is made of a deformable metal which may be inelastically deformed into the closed position. Proximal extremity 116 has an inner surface 122 which faces an outer surface 124 of clip body 112 in the closed position. Adjacent to the base of distal extremity 114, inner surface 122 is preferably spaced apart from outer surface 124 in the closed position by no more than the combined thickness of all tissue layers to which the clip is to be applied so as to compress the tissue therebetween. Proximal extremity 116 also has an outer side 126 which is configured to shield distal point 118, preferably having a shape and dimension substantially the same as that of distal extremity 114 so that outer side 126 lies adjacent and parallel to a substantial portion of distal extremity 114 in the closed position. Clip body 112 has a proximal side 127 which facilitates closure of the clip, as described below.

The use of clip 110 with a clip applier 128 is illustrated in FIGS. 8A–8B. Clip applier 128 may have a construction like that of clip applier 42 of FIGS. 2–3, having an outer shaft 130 with a lumen 132 extending through it, and an inner shaft 134 disposed within lumen 132 over which outer shaft 130 is slidable. An actuator handle (not shown) like that shown in FIGS. 2A–2C is provided at the proximal end of inner shaft 134 and is coupled to outer shaft 130 such that actuation of the handle translates outer shaft 130 distally. A clip holding mechanism 136 is fixed to the distal end of inner shaft 134 and includes a recessed area 138 configured to receive proximal extremity 116 of clip 110, and a transverse pin 140 configured to extend through aperture 120. A shelf 142 along an inner edge of recessed area 138 prevents rotation of clip 110 about pin 140. In this way, clip 110 is held with distal extremity 114 extending generally in the radial direction from the longitudinal axis of inner shaft 134. A clip cover 144 is slidably mounted within lumen 132 parallel to a distal portion of inner shaft 134 and is movable from a proximal position shown in FIGS. 8A–8B to a distal position in which the clip cover extends over proximal extremity 116 of clip 110 to retain it on pin 140. A spring 146 within lumen 132 engages the proximal end of clip cover 144 and biases it into the distal position.

When the actuator handle of clip applier 128 is actuated, outer shaft 130 is advanced distally so that its distal end engages proximal side 127 of clip 110, thereby deforming the clip into the closed position shown in FIG. 8B. Distal extremity 114 is driven in a generally rotational manner about an axis located roughly at the junction between proximal extremity 116 and clip body 112. Recess 138 is configured to allow distal extremity 114 to be moved completely into the closed position without interference with inner shaft 134. After closure, clip cover 144 may be retracted away from holding mechanism 136 and clip 110 then released from pin 140.

Figure 9B:
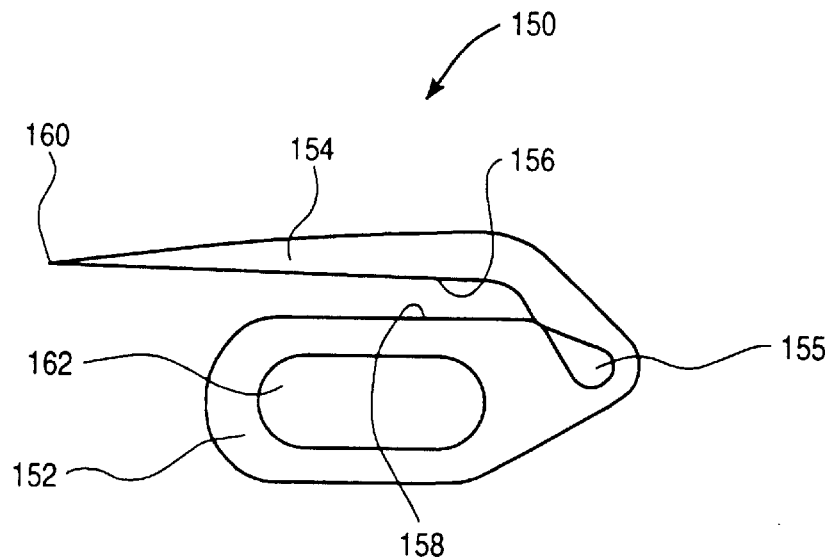
FIGS. 9A–9B are front elevational views of a fourth embodiment of a surgical clip constructed in accordance with the principles of the invention in an open and a closed position, respectively.
Figure 9A:
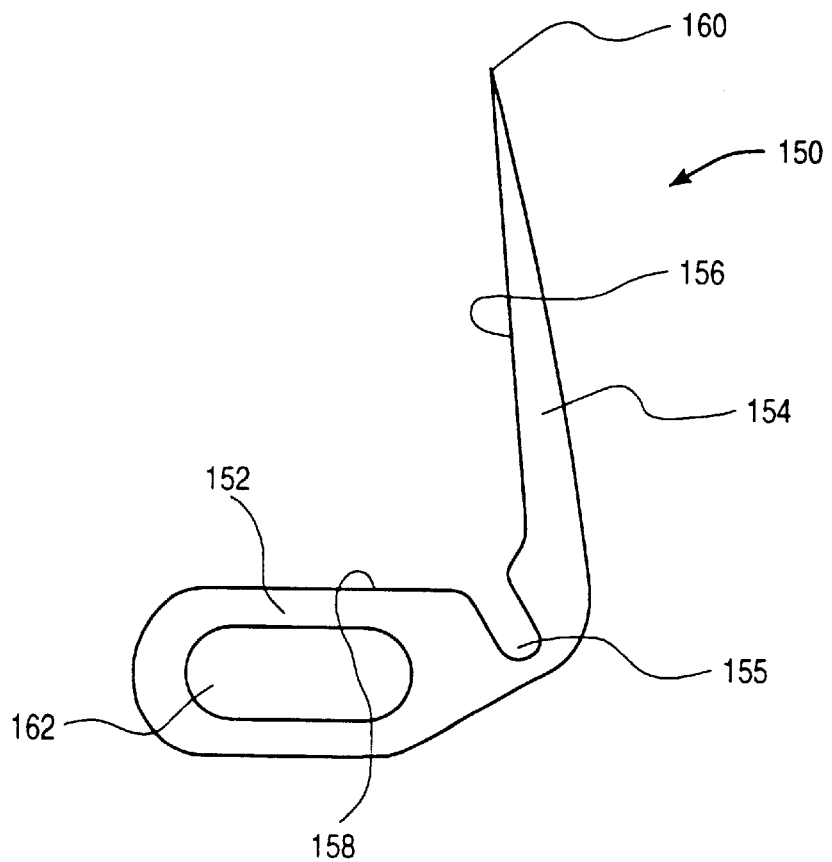

Still another embodiment of a surgical clip according to the invention is illustrated in FIGS. 9A–9B. Surgical clip 150 includes a proximal extremity 152 and a distal extremity 154. Distal extremity 154 has a sharp distal point 160 for penetrating tissue. Proximal extremity 152 includes an aperture 162 to facilitate holding clip 150 in a clip applier, as described below. Distal extremity 154 is movable between the open position of FIG. 9A and the closed position of FIG. 9B. A notch 155 is disposed at the junction of the distal and proximal extremities which causes distal extremity 154 to pivot in a hinge-like manner about an axis passing generally through the base of the notch when a transverse force is applied to distal extremity 154. Clip 150 is preferably made of a deformable metal so as to remain in the closed position when closure force is released. Distal extremity 154 has an inner surface 156 which faces an outer surface 158 of proximal extremity 152. In the closed position, at a point adjacent to the junction of the distal and proximal extremities, inner surface 156 is preferably separated from outer surface 158 by less than the combined thickness of the tissue layers to which clip 150 is to be applied, so as to compress the tissue between the distal and proximal extremities. It is most preferred that notch 155 be configured to allow the edges of the tissue to reside within the notch, such that when the clip is closed, the layers of tissue will be compressed within the notch itself.

A distal portion of an applier 164 for closing clip 150 is illustrated in FIGS. 10A–10D. Applier 164 includes an outer shaft 166 having a lumen 168, and an inner shaft 170 over which outer shaft 166 is slidable. An actuator handle like that described above in connection with FIGS. 2A–2C is attached to the proximal end of inner shaft 170 and coupled to outer shaft 166 such that actuation of the handle moves outer shaft 166 proximally relative to inner shaft 170. Thus, for this embodiment, links 66 of FIGS. 2A–2C will be oriented such that the outer ends pinned to leaves 66 are distal to the inner ends pinned to outer shaft 166, thereby pulling the outer shaft proximally when the leaves are pivoted inwardly. In this embodiment, outer shaft 166 is rotatably mounted to collar 67 so as to be rotatable relative to inner shaft 170 for reasons which will become apparent below.

A clip holding mechanism 172 is attached to the distal end of inner shaft 170 and includes a pair of transverse pins 174 over which clip 150 may be placed. A clip cover 176 is slidably mounted in parallel to a distal portion of inner shaft 170 and is biased distally by a spring 178 disposed within lumen 168 which engages the proximal end of the clip cover. In this way, after a clip is placed on pins 174 with clip cover 176 in the retracted position shown, clip cover 176 is allowed to return to a distal position covering proximal extremity 152 of the clip so as to retain it on pins 174.

An anvil 180 extends distally from a distal end of outer shaft 166 and has a transverse end 182 generally orthogonal to a longitudinal axis of the outer shaft (and generally parallel to the axis of movement of distal extremity 154). In order to facilitate penetrating distal extremity 154 through the tissue to which the clip is to be applied, anvil 180 is initially positioned proximally of distal extremity 154 as shown in FIG. 10A by maintaining leaves. Alternatively, anvil 180 itself may be mounted to outer shaft 166 so as to be pivotable or rotatable to a position suitably distant from distal extremity 154. Anvil 180 is positioned so that transverse end 182 may be positioned distally of and generally perpendicular to distal extremity of 154 of the clip, as illustrated in FIGS. 10A–10B. In this way, when the actuator handle of applier 164 is actuated, transverse end 182 is drawn in the proximal direction, engaging distal extremity 154 and deforming it into the closed position shown in FIG. 10C.

Figure 11A:
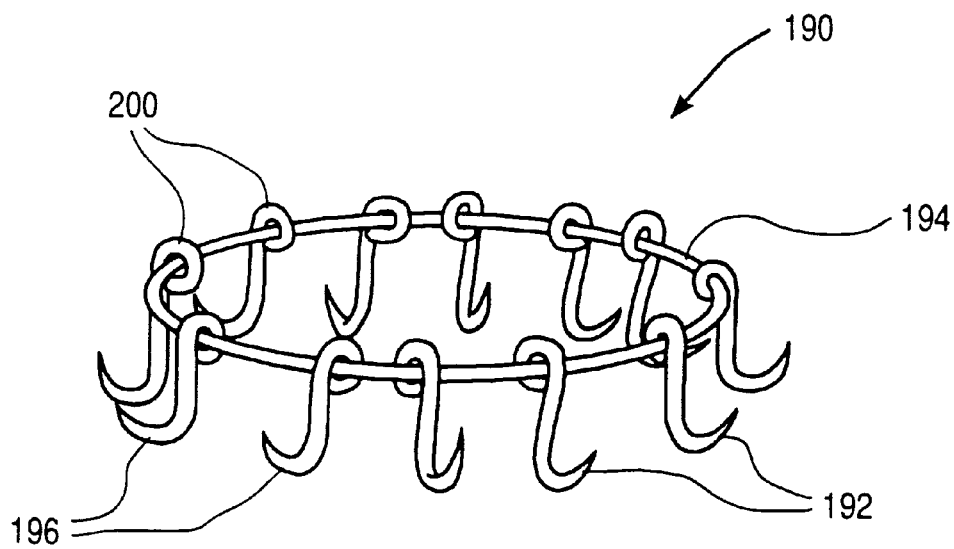
FIGS. 11A–11B are perspective views of two embodiments of an anastomosis clip system constructed in accordance with the principles of the invention.
Figure 11B:
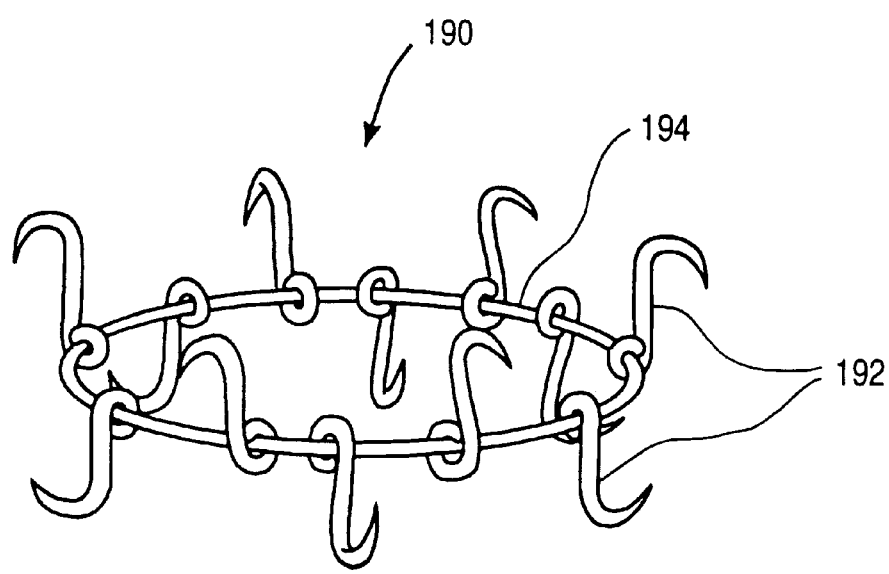
Figure 12A:
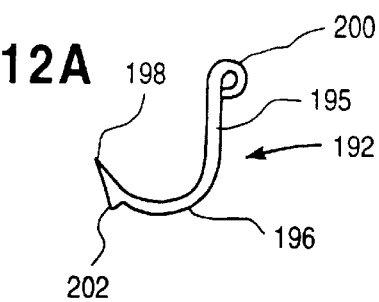
FIGS. 12A–12F are front views of various embodiments of anastomosis clips useful in the anastomosis clip system of FIGS. 11A–11B.

A surgical clip system according to the invention is illustrated in FIGS. 11A–11B. Clip system 190 includes plurality of clips 192 coupled to a flexible band 194. Clips 192 include, as shown in FIG. 12A, a proximal extremity 195, a needle portion 196 having a sharp distal point 198 for penetrating tissue, and a coupling 200 for attachment to band 194. Needle portion 196 is preferably curved or J-shaped with its distal end being at an angle of no more than about 90, and preferably about 45–85 relative to proximal extremity 195. Preferably, coupling 200 comprises a loop, eyelet, or other structure through which band 194 may be inserted that allows clip 192 to slide along band 194. Alternatively, coupling 200 may be configured to non-movably attach clip 192 to the band, such as by clamping or crimping onto the band, by bonding or welding the coupling to the band, or by allowing the band to be knotted or looped through the coupling. Needle portion 196 preferably includes a barb 202 which prevents the needle portion from being removed from the tissue to which it is applied.

Band 194 is a flexible biocompatible material such as suture or an elastomeric or metallic strap, band or cable. Band 194 is preferably a continuous annular ring, but may also be a non-continuous or broken ring biased into a generally annular shape, with a retainer on each end to retain clips 192 on the band. Usually the shape of band 194 will be circular, but could alternatively be a variety of other non-circular shapes including elliptical, egg-shaped, cobra head-shaped, oval, or the like. In any case, the flexibility of the band allows it to conform to whatever shape is desirable for the particular vascular structures with which it is being used. Clips 192 may be mounted to band 194 with the all needle portions 196 pointing outward as shown, or with some of needle portions 196 pointing inward. As shown in FIG. 11B, clips 192 may also be attached to band 194 so that some extend upward from the band, while others extend downward from the band.

Figure 12B:
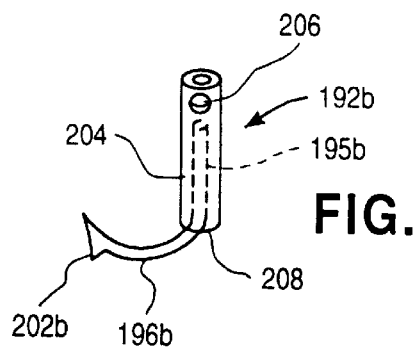

FIGS. 12B–12G illustrate various alternative embodiments of clips for use in clip system 190. In FIG. 12B, a length of hypotube 204 is mounted over proximal extremity 195B. A hole 206 is disposed near the proximal end of hypotube 204 through which band 194 may be inserted. The distal end 208 of hypotube 204 engages the tissue through which needle portion 196B is inserted and prevents its movement upward along proximal extremity 195B. Preferably, the length of hypotube 204 is selected so that the distance between distal end 208 and barb 202B is less than the combined thickness of the tissue layers through which needle portion 196B is inserted so that the tissue is compressed between the hypotube and the barb.

Figure 12C:
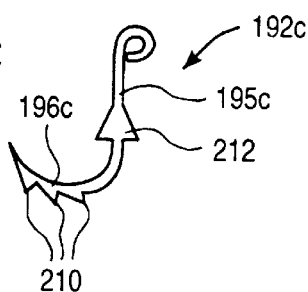

In FIG. 12C, clip 192C has a plurality of barbs 210 arranged sequentially along needle portion 196C. A stop 212 is disposed on proximal extremity 195C. In this way, the layers of tissue to which clip 192C is applied may be translated along needle portion 196C until the outer layer contacts stop 212. Barbs 210 prevent the tissue from moving away from stop 212. Preferably, the distance between stop 212 and barbs 210 is less than the combined thickness of the tissue to allow the tissue to be compressed between the stop and the barbs.

Figure 12D:
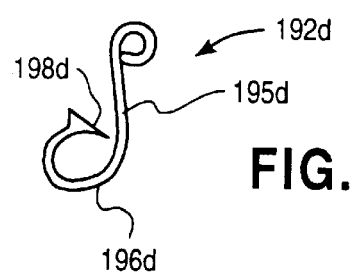

In FIG. 12D, clip 192D has a configuration like clip 192 of FIG. 12A, but in this embodiment the clip is constructed of a shape memory alloy such as Nitinol (Raychem Corp.). At body temperature the clip has a closed shape in which distal point 198D is close to or contacting proximal extremity 195D so as to define an enclosed space in which the tissue is retained. The clip may be isothermally transformed from an open to a closed shape by using needle drivers or other suitable instruments to hold distal point 198D away from proximal extremity 195D then release the distal point after it has been applied to tissue. Preferably, however, the clip is thermally transformed by heating the clip to the material's transition temperature using a heated probe or needle driver until the clip assumes the closed shape.

Figure 12E:
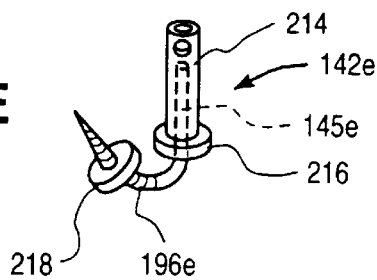

In FIG. 12E, clip 192E has a hypotube 214 mounted to proximal extremity 195E as in FIG. 12B, and includes a retainer 216 mounted to proximal extremity 195E which abuts the distal end of hypotube 214. A distal retainer 218 is threadably or slidably received over needle portion 196E which may be placed on the needle portion after it has been applied to the tissue. The tissue may be advanced along needle portion 196E until it engages retainer 216, and distal retainer 218 then moved into contact with the opposing side of the tissue to compress it between the two retainers.

Figure 12F:
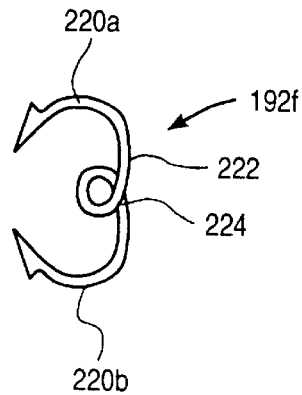
Figure 12G:
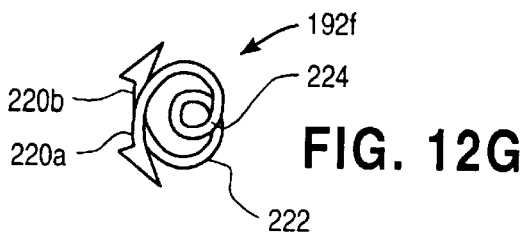
FIG. 12G is a front view of the anastomosis clip of FIG. 12F in a closed position.

In FIGS. 12F–G, clip 192F has a pair of opposing needle portions 220A, 220B connected by a bridging segment 222. Bridging segment 222 may include a loop 224 which enhances deflection of needle portions 220. Clip 192F is movable from the open configuration of FIG. 12F to the closed configuration of FIG. 12G wherein needle portion 220A, 220B cross over one another to define an enclosed space in which the tissue may be retained. Preferably, clip 192F is made of a superelastic shape memory alloy such as Nitinol. In one embodiment, the clip is biased into the closed configuration at ambient and body temperature, and is isothermally held open using appropriate instruments to apply needle portions 220 to the target tissue, then released to allow the clip to close. In an alternative embodiment, the material has a transition temperature above ambient temperature at which it resumes the closed shape from the open shape. In this way, after clip 192F has been applied to tissue in the open configuration, heat may be applied to the clip using a heating probe or heated forceps to cause it to assume the closed configuration.

It should be understood that the embodiments illustrated in FIGS. 12A–12G are only exemplary of the wide variety of clips that may be used in the surgical clip system of the invention. Moreover, any of the clips illustrated in FIGS. 1–10 above may be used in clip system 190 of FIGS. 11A–11B by, for example, providing an additional aperture in the clip body through which band 194 may extend.

Figure 13A:
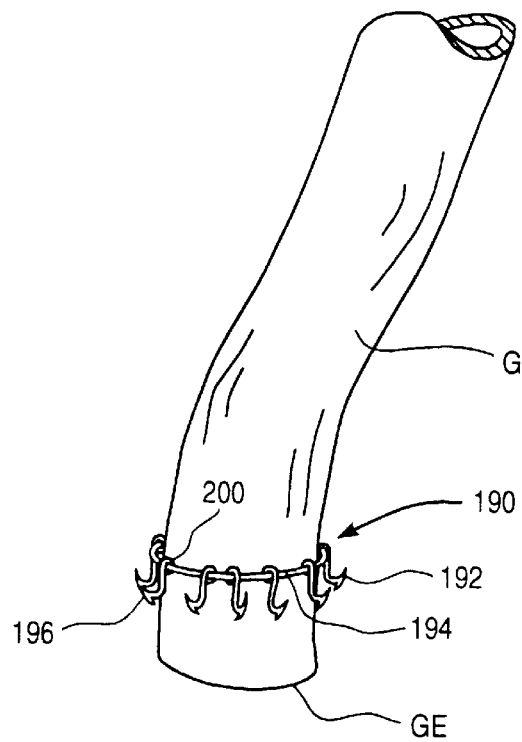
FIGS. 13A–13C are perspective views of the anastomosis clip system of FIG. 11A schematically illustrating the use of the anastomosis clip system for the anastomosis of a graft vessel to a target vessel.
Figure 13B:
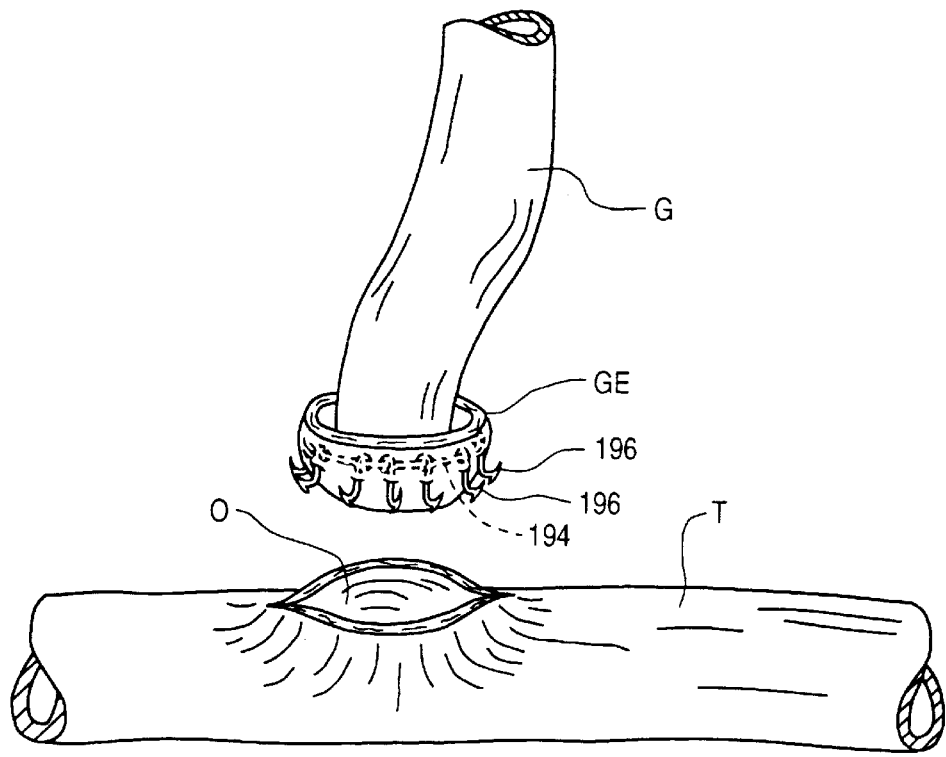
Figure 13C:
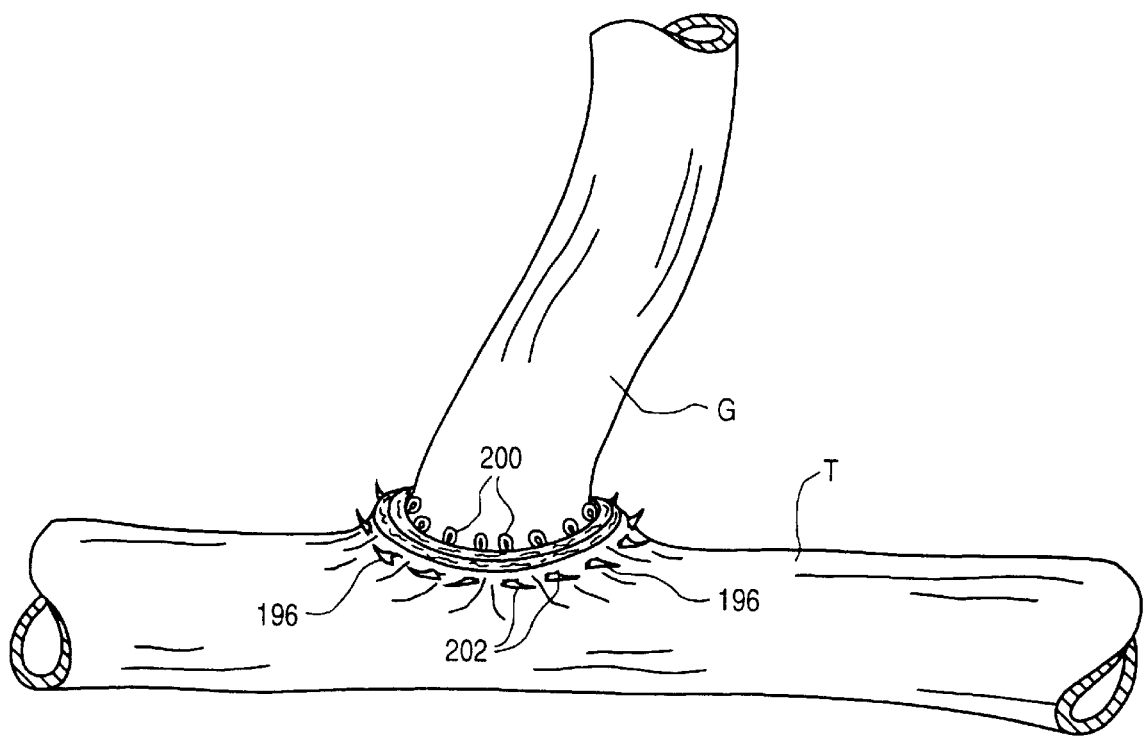

FIGS. 13A–13C illustrate the use of clip system 190 in the anastomosis of a graft vessel G to a target vessel T. Initially, band 194 to which clips 192 are coupled is placed over the end GE of graft vessel G. Vessel end GE is then everted over clips 192 to allow each needle portion 196 to penetrate the graft vessel wall from the exterior surface of the vessel toward the interior surface (which now faces outwardly) as shown in FIG. 13B. Clips 192 may be repositioned along band 194 as needed to allow selection of the optimum location at which each needle portion 196 penetrates the graft vessel wall based on the shape and condition of the vessel. An opening O is formed in the target vessel wall corresponding to the size and shape of everted graft vessel end GE using a surgical knife or scissors. Everted graft vessel end GE is then inserted into opening O and the edges of vessel end GE are approximated with the edges of opening O. Each needle portion 196 is then grasped with surgical needle drivers or forceps and penetrated through the wall of target vessel T from the interior toward the exterior thereof. The autonomy of each clip 192, the flexibility of band 194 and the compliance of graft vessel G allow each clip 192 to be manipulated and positioned to penetrate the target vessel wall at the optimum location according to the shape and condition of the vessel. Needle portions 196 are inserted through the target vessel wall until barbs 202 pass through to the exterior of the vessel. The vessel walls are thus compressed between barbs 202 and proximal extremities 195, providing a secure and hemostatic connection. Optionally, band 194 may then be severed and removed from clip couplings 200. This ensures that each clip is completely autonomous and unrestricted by the other clips, providing a compliant anastomosis comparable to a sutured anastomosis.

Figure 14C:
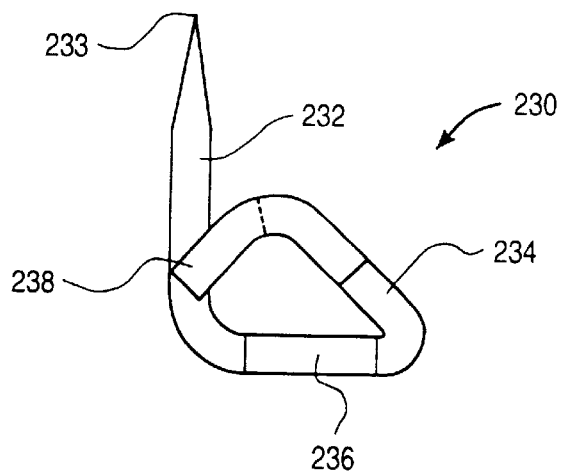
FIGS. 14A and 14C are front views of a further embodiment of a surgical clip according to the invention in an open and a closed position, respectively.
Figure 14A:
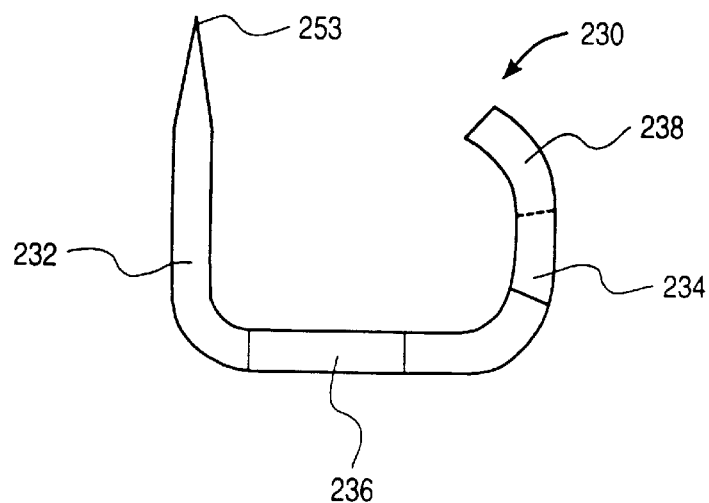
Figure 14B:
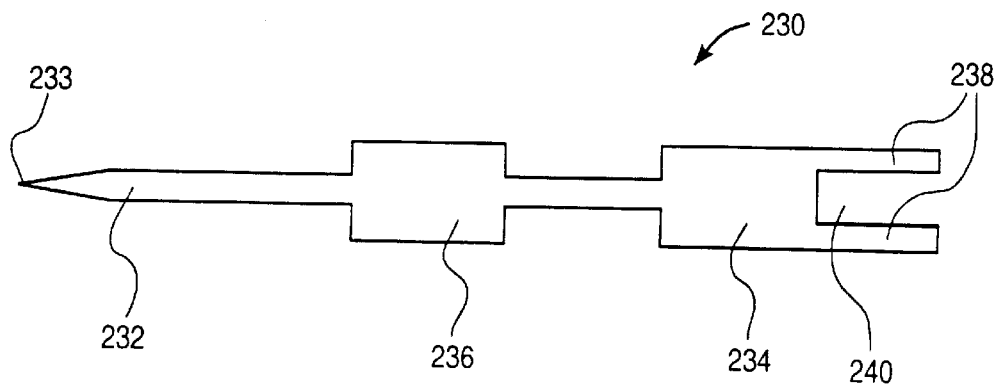
FIGS. 14B is a top view of the surgical clip of FIG. 14A in a straightened configuration.

An additional embodiment of a surgical clip according to the invention is illustrated in FIGS. 14A–14C. In this embodiment, surgical clip 230 may be formed by cutting out a two-dimensional pattern from a flat piece of material as shown in FIG. 14B, making the clip more simple and economical to manufacture. Clip 230 has a distal extremity 232, a proximal extremity 234, and a flanged central portion 236 therebetween which has a transverse width substantially wider than the distal extremity. Distal extremity 232 has a distal point 233 configured to penetrate tissue. Proximal extremity 234 is bifurcated into two spaced-apart segments 238 defining an opening 240 therebetween in which distal extremity 232 may be received in the closed position of FIG. 14C. Distal extremity 232 is disposed at an angle of about 30°–120°, preferably about 60°–120°, relative to flanged central portion 236. Proximal extremity 234 is preferably at an angle of at least about 90° relative to flanged central portion 236 to facilitate closure of the clip in the manner described below.

Figure 15A:
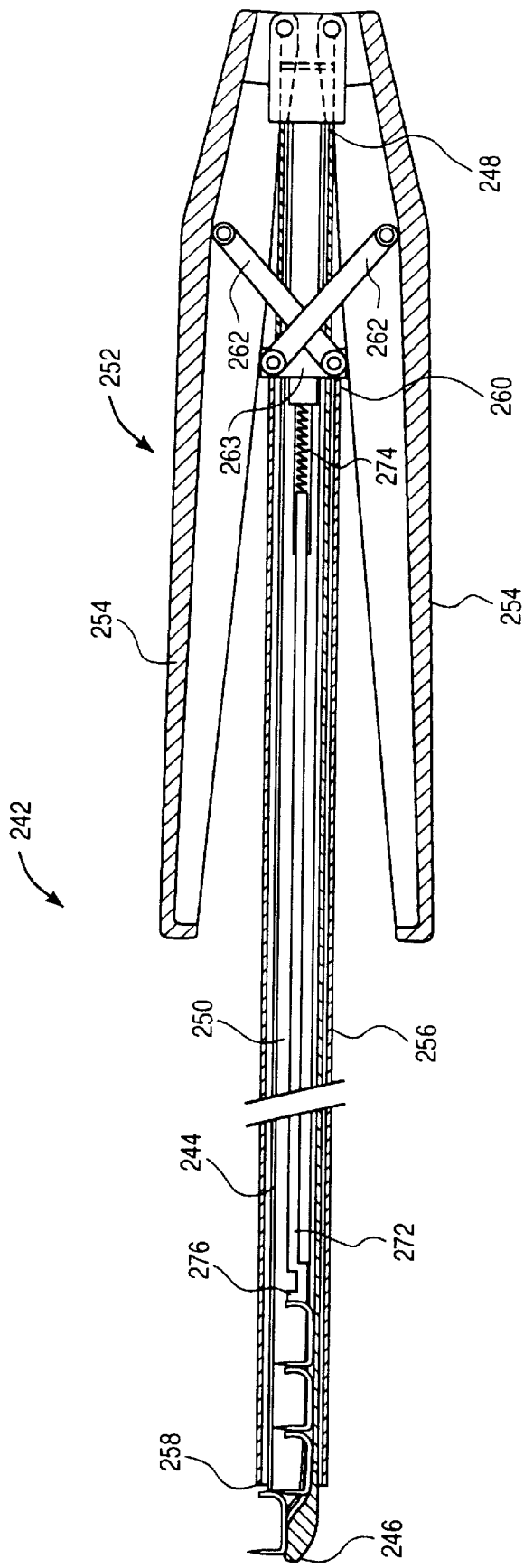
FIG. 15A is a side cross-sectional view of a clip applier for applying the surgical clip of FIGS. 14A–14C.

Flanged central portion 236 is configured to be held by an applier 242, illustrated in FIGS. 15A–15C. Applier 242 is preferably adapted for holding a plurality of clips 230 simultaneously and automatically feeding and applying the clips in succession. Applier 242 has an inner shaft 244 having a distal end 246, a proximal end 248 and a lumen 250 therebetween. An actuator 252 is mounted to the proximal end 248, and has a pair of pivotable leaves 254 extending distally and outwardly therefrom. An outer shaft 256 is slidably disposed over inner shaft 244 and has a distal end 258 and a proximal end 260. A pair of links 262 are pinned at their outer ends to leaves 254 and at their inner ends to a collar 263 attached to proximal end 260 of outer tube 256. In this way, when the user pivots leaves 254 inwardly, outer shaft 256 is translated distally relative to inner shaft 244. A flat spring (not shown) may be mounted to leaves 254 to bias them in the outward position, or a tension spring (not shown) may be mounted to outer shaft 256 to bias it in the proximal direction.

Inner shaft 244 has an axial channel 266 along one side of inner lumen 250 configured to slidably receive a plurality of clips 230. As illustrated in FIG. 15B, channel 266 has a width wide enough to receive flanged central portions 236 of clips 230. A wall 268 separates channel 266 from lumen 250 and has a slot 270 narrower than flanged central portions 236, but wide enough to allow distal extremities 232 and proximal extremities 234 to slide axially. In this way, a plurality of clips 230 may be lined up end to end in channel 266, with the distal extremity of each clip abutting the proximal extremity of an adjacent clip. A pusher 272 is mounted to the proximal end of inner shaft 244 and is biased distally by spring 274. Pusher 272 has a distal end 276 configured to push against the most proximal clip in channel 266, thereby urging all of clips 230 toward distal end 246.

Channel 266 is angled laterally as it approaches distal end 246, and terminates at an abutment 278 against which the distal most clip 230' is positioned. This exposes most of distal extremity 232' to facilitate applying it to one or more layers of tissue, and positions proximal extremity 234' adjacent to distal end 258 of outer shaft 256. In this way, when actuator 252 is actuated, outer shaft 256 engages proximal extremity 234' of clip 230' and urges it into the closed position of FIG. 14C. As shown in FIG. 15C, slot 270 widens at the distal end of channel 266 to a width wider than flanged central portion 236', allowing clip 230' to be withdrawn from channel 266 after it has been closed. When clip 230' has been withdrawn, the next clip in line is urged distally by pusher 272 until it contacts abutment 278, where it is ready for application. Thus, a plurality of clips may be applied successively to a surgical site within a body cavity without removing the applier from the body cavity to reload clips.

Clip applier 242 may be preloaded with a plurality of clips 230 and disposed of upon application of all of the clips. Alternatively, inner shaft 244 may be detachable from actuator 252, allowing the actuator and outer shaft to be sterilizable and reusable, with inner shaft 244 being replaced or reloaded with clips between uses. In addition, clip applier 242 is preferably configured for endoscopic uses, having a length and profile suitable for positioning through a trocar sleeve or other small percutaneous access port into a body cavity.

While the above is a complete description of the preferred embodiments of the invention, various alternatives, substitutions, modifications, and equivalents of the embodiments described are possible without departing from the principles thereof. Therefore, nothing disclosed above should be taken to limit the scope of the invention, which is defined by the appended claims.

What is claimed is:

1. A surgical clip for sealingly joining a graft vessel to a target vessel, the graft vessel having a graft vessel wall defining a graft lumen, the target vessel having a target vessel wall defining a target lumen, the surgical clip comprising:
   a clip body;
   a needle portion extending from the clip body and having a distal end configured to penetrate the graft and target vessel walls and extend outside of the graft and target vessels, the clip body being configured to prevent passage of the clip body through the graft and target vessel walls; and
   a retainer disposed outside of the graft and target vessels for retaining the graft and target vessel walls on the needle portion, the retainer being configured to compress the graft vessel wall against the target vessel wall, the retainer having an inner surface and the clip body having an outer surface which faces the inner surface in the closed position, the retainer being configured to compress the graft and target vessel walls between the inner and outer surfaces.

2. The surgical clip of claim 1 wherein the needle portion is disposed at an angle of no more than about 120° relative to the outer surface of the clip body in the open position.

3. A surgical clip for sealingly joining a graft vessel to a target vessel, the graft vessel having a graft vessel wall defining a graft lumen, the target vessel having a target vessel wall defining a target lumen, the surgical clip comprising:
   a clip body;
   a needle portion extending from the clip body and having a distal end configured to penetrate the graft and target vessel walls and extend outside of the graft and target vessels, the clip body being configured to prevent passage of the clip body through the graft and target vessel walls; and
   a retainer disposed outside of the graft and target vessels for retaining the graft and target vessel walls on the needle portion, wherein the retainer comprises a leg attached to the clip body movable between an open position spaced apart from the needle portion and a closed position closer to the needle portion for retaining the graft and target vessel walls thereon, wherein an end portion of the retainer is configured to extend across the needle portion in the closed position.

4. The surgical clip of claim 3 wherein the retainer has two generally parallel segments for extending across the needle portion on opposing sides thereof and a slot between the parallel segments for receiving the needle portion.

5. A surgical clip for sealingly joining a graft vessel to a target vessel, the graft vessel having a graft vessel wall defining a graft lumen, the target vessel having a target vessel wall defining a target lumen, the surgical clip comprising:
   a clip body;
   a needle portion extending from the clip body and having a distal end configured to penetrate the graft and target vessel walls and extend outside of the graft and target vessels, the clip body being configured to prevent passage of the clip body through the graft and target vessel walls; and
   a retainer disposed outside of the graft and target vessels for retaining the graft and target vessel walls on the needle portion, wherein the retainer comprises a leg attached to the clip body movable between an open position spaced apart from the needle portion and a closed position closer to the needle portion for retaining the graft and target vessel walls thereon, wherein the retainer shields the distal end of the needle portion in the closed position.

6. A surgical clip for sealingly joining a graft vessel to a target vessel, the graft vessel having a graft vessel wall defining a graft lumen, the target vessel having a target vessel wall defining a target lumen, the surgical clip comprising:
   a clip body including a middle portion configured to be held by a clip applier for applying the clip, wherein the middle portion has an aperture therein for receiving a portion of the clip applier;
   a needle portion extending from the clip body and having a distal end configured to penetrate the graft and target vessel walls and extend outside of the graft and target vessels, the clip body being configured to prevent passage of the clip body through the graft and target vessel walls; and
   a retainer disposed outside of the graft and target vessels for retaining the graft and target vessel walls on the needle portion.

7. A surgical clip for sealingly joining a graft vessel to a target vessel, the graft vessel having a graft vessel wall defining a graft lumen, the target vessel having a target vessel wall defining a target lumen, the surgical clip comprising:
   a clip body including a coupling for attachment to a flexible band;
   a needle portion extending from the clip body and having a distal end configured to penetrate the graft and target vessel walls and extend outside of the graft and target vessels, the clip body being configured to prevent passage of the clip body through the graft and target vessel walls; and
   a retainer disposed outside of the graft and target vessels for retaining the graft and target vessel walls on the needle portion.

8. An anastomosis device for sealingly joining a graft vessel to a target vessel, the graft vessel having a free end and a graft vessel wall defining a graft lumen, the target vessel having a target vessel wall with an opening therein and defining a target lumen, the anastomosis device comprising:
   a flexible ring-shaped band defining a central opening in which the graft vessel may be received; and
   a plurality of clips coupled to the band and positionable at spaced apart locations around the band, each clip having a first portion for engaging the graft vessel wall and a second portion for engaging the target vessel wall, the first and second portions being configured to retain the graft vessel wall in sealing engagement with the target vessel wall.

9. The anastomosis device of claim 8 wherein the clip has a distal extremity for penetrating the graft and target vessel walls.

10. The anastomosis device of claim 9 further comprising a retainer for retaining the graft and target vessel walls on the distal extremity.

11. The anastomosis device of claim 10 wherein the retainer comprises at least one barb on the distal extremity.

12. The anastomosis device of claim 9 wherein the clip is generally hook-shaped, the distal extremity being oriented at an angle of at least about 90° relative to a proximal portion of the clip.

13. The anastomosis device of claim 9 wherein at least a portion of the clip is movable between an open and a closed position so as to retain the graft and target vessel walls on the distal extremity.

14. The anastomosis device of claim 13 wherein the movable portion of the clip is configured to remain outside of the graft and target vessels when the distal extremity has penetrated the graft and target vessel walls.

15. The anastomosis device of claim 14 wherein the distal extremity has a distal end, the distal end being configured to be disposed outside the graft and target vessels when the distal extremity has penetrated the graft and target vessel walls.

16. The anastomosis device of claim 13 wherein the movable portion of the clip is deformable from the open position to the closed position.

17. The anastomosis device of claim 13 wherein the movable portion is spaced apart from the distal extremity in the open position and is closer to the distal extremity in the closed position.

18. The anastomosis device of claim 13 wherein the distal extremity is movable between the open and closed positions.

19. The anastomosis device of claim 8 wherein the clip has a loop for slidably receiving the band.

20. An anastomosis system for sealingly joining a graft vessel to a target vessel, the graft vessel having a free end and a graft vessel wall defining a graft lumen, the target vessel having a target vessel wall with an opening therein and defining a target lumen, the anastomosis system comprising:
    at least one anastomosis clip including a clip body having a distal extremity with a distal end and a proximal extremity with a proximal end, the distal end being configured to penetrate through the graft and target vessel walls; and
    a clip applier including a holding mechanism for releasably holding the anastomosis clip such that the distal end may be passed through the graft vessel wall near the free end and through the target vessel wall near the opening such that both the distal and proximal ends of the clip body are outside the graft and target vessels, and a shaping mechanism disposed outside the graft and target vessels for shaping at least a portion of the clip body so as to compress the graft wall against the target vessel wall with the target vessel lumen in communication with the graft vessel lumen.

21. The anastomosis system of claim 20 wherein the proximal extremity comprises a leg extending from the clip body movable between an open position spaced apart from the distal extremity and a closed position closer to the distal extremity.

22. The anastomosis system of claim 21 wherein the proximal extremity shields the distal end of the distal extremity in the closed position.

23. The anastomosis system of claim 20 wherein the distal extremity is movable from an open position spaced apart from the proximal extremity and a closed position closer to the proximal extremity.

24. The anastomosis system of claim 23 wherein the distal extremity has an inner surface and the clip body has an outer surface which faces the inner surface in the closed position, the distal extremity being configured to compress the graft and target vessel walls between the inner and outer surfaces in the closed position.

25. The anastomosis system of claim 24 wherein the inner surface of the distal extremity is disposed at a an angle of no more than about 120° relative to the outer surface of the clip body in the open position.

26. The anastomosis system of claim 20 wherein the clip body includes a middle portion configured to be held by the clip applier.

27. The anastomosis system of claim 26 wherein the middle portion has a substantially larger cross-sectional area than the distal extremity.

28. The anastomosis system of claim 27 wherein the clip applier has a pin on a distal end thereof and wherein the middle portion of the clip body has an aperture therein for receiving the pin.

29. The anastomosis system of claim 26 wherein the holding mechanism is configured to hold the middle portion in a stationary position relative to the clip applier as the shaping mechanism shapes the clip body.

30. The anastomosis system of claim 20 wherein the clip applier is configured to hold a plurality of clips.

31. The anastomosis system of claim 30 wherein the clip applier has an axial channel and the clip has a middle portion having a width wider than the distal extremity, the middle portion being configured to be axially slidable along the axial channel.

32. The anastomosis clip of claim 20 wherein the clip applier has an inner shaft and an outer shaft movable with respect to each other, the clip body being held by a first of either the inner or the outer shaft and the clip body being shaped by a second of either the inner or the outer shaft.

33. A method of sealingly joining a graft vessel to a target vessel, the graft vessel having a free end and a graft vessel wall defining a graft lumen, the target vessel having a target vessel wall defining a target lumen and having an opening therein, the method comprising:
    providing a plurality of anastomosis clips each including a clip body having a distal extremity with a distal end and a proximal extremity with a proximal end;
    penetrating the graft vessel wall and the target vessel wall with the distal extremity of each anastomosis clip such that the distal and proximal ends are disposed outside of the graft and target vessels; and
    shaping a portion of each clip body outside of the graft and target vessels so as to compress the graft vessel wall against the target vessel wall with the graft lumen in communication with the target lumen.

34. The method of claim 33 wherein the shaping step comprises moving the proximal extremity of the clip body from an open position spaced apart from the distal extremity to a closed position closer to the distal extremity.

35. The method of claim 33 wherein the shaping step comprises moving the distal extremity of the clip body from an open position spaced apart from the distal extremity to a closed position closer to the distal extremity.

36. The method of claim 33 wherein the shaping step comprises generally inelastically deforming a portion of the clip body.

37. The method of claim 33 wherein the shaping step comprises compressing the graft and target vessel walls between an inner surface of the distal extremity and an outer surface of the proximal extremity.

38. The method of claim 33 further comprising shielding the distal end of the distal extremity outside the graft and target vessels after penetrating the graft and target vessel walls.

39. The method of claim 33 wherein the target vessel comprises a coronary artery on the heart.

40. The method of claim 39 wherein the graft vessel comprises a vessel selected from the group including mammary arteries, vein grafts, arterial grafts, and artificial grafts.

41. The method of claim 33 wherein the step of penetrating comprises, after penetrating the graft vessel wall, selecting a position for penetrating the target vessel wall, and positioning the distal extremity relative to the target vessel wall so as to penetrate the target vessel wall at said position.

42. The method of claim 33 wherein the step of penetrating is performed without continually maintaining the graft vessel wall in contact with the target vessel wall.

43. The method of claim 42 further comprising positioning the graft vessel wall relative to the target vessel wall after penetrating the graft vessel wall but before penetrating the target vessel wall.

44. The method of claim 43 wherein the target vessel is in a body cavity, the step of penetrating comprising penetrating the graft vessel wall outside the body cavity, positioning the graft vessel in the body cavity, and penetrating the target vessel wall in the body cavity.

45. The method of claim 43 wherein the target vessel is in a body cavity, the step of shaping being performed with an elongated instrument positioned in the body cavity through a percutaneous penetration.

46. The method of claim 45 wherein the elongated instrument is positioned through a tubular cannula into the body cavity.

47. The method of claim 45 wherein the elongated instrument comprises a clip applier.

48. The method of claim 47 further comprising repeating the steps of penetrating and shaping for a plurality of anastomosis clips without removing the clip applier from the body cavity.

* * * * *